US011135120B2

(12) United States Patent
Arzanpour et al.

(10) Patent No.: US 11,135,120 B2
(45) Date of Patent: Oct. 5, 2021

(54) SYSTEM AND DEVICE FOR GUIDING AND DETECTING MOTIONS OF 3-DOF ROTATIONAL TARGET JOINT

(71) Applicant: Human In Motion Robotics Inc., North Vancouver (CA)

(72) Inventors: Siamak Arzanpour, North Vancouver (CA); Soheil Sadeqi, Vancouver (CA); Shaun Bourgeois, Creston (CA); Jung Wook Park, Surrey (CA)

(73) Assignee: HUMAN iN MOTiON RObOTiCs INC., North Vancouver (CA)

( * ) Notice: Subject to any disclaimer, the term of this patent is extended or adjusted under 35 U.S.C. 154(b) by 360 days.

(21) Appl. No.: 15/778,467

(22) PCT Filed: Jan. 16, 2017

(86) PCT No.: PCT/CA2017/050046
§ 371 (c)(1),
(2) Date: May 23, 2018

(87) PCT Pub. No.: WO2017/120680
PCT Pub. Date: Jul. 20, 2017

(65) Prior Publication Data
US 2018/0325766 A1 Nov. 15, 2018

Related U.S. Application Data

(60) Provisional application No. 62/279,798, filed on Jan. 17, 2016.

(51) Int. Cl.
*A61H 3/00* (2006.01)
*A61B 5/00* (2006.01)
(Continued)

(52) U.S. Cl.
CPC .............. *A61H 3/00* (2013.01); *A61B 5/1107* (2013.01); *A61B 5/1121* (2013.01); *A61B 5/389* (2021.01);
(Continued)

(58) Field of Classification Search
CPC ... A61B 5/1107; A61B 5/1121; A61B 5/4519; A61B 5/4528; A61B 5/4571;
(Continued)

(56) References Cited

U.S. PATENT DOCUMENTS 5,282,460 A * 2/1994 Boldt .................. A61F 2/68
601/5
5,476,441 A * 12/1995 Durfee ................. A61F 5/0102
434/112

(Continued)

OTHER PUBLICATIONS

International Search Report and Written Opinion in corresponding International Patent Application No. PCT/CA2017/050046, dated Mar. 29, 2017, in 8 pages.

*Primary Examiner* — Justine R Yu
*Assistant Examiner* — Matthew D Ziegler

(57) ABSTRACT

Examples of a device for guiding and detecting a motion of a target joints and a motion assistance system such motion guiding devices are described. The motion guiding and detecting device comprises a motion generator and a motion transfer and target interfacing unit to transfer the motion generated by the motion generator to the target joint. The system further includes a motion detection and feedback unit that interfaces with the target, and a controller that interfaces (Continued)

with both the feedback unit and the motion generator to control and coordinate the motion of the motion generator and the target joint.

25 Claims, 26 Drawing Sheets

(51) Int. Cl.
| | |
|---|---|
| A61F 5/01 | (2006.01) |
| A61B 5/11 | (2006.01) |
| A61H 1/02 | (2006.01) |
| A61F 2/72 | (2006.01) |
| A61F 2/70 | (2006.01) |
| A61B 5/389 | (2021.01) |

(52) U.S. Cl.
CPC .......... *A61B 5/4528* (2013.01); *A61B 5/4571* (2013.01); *A61B 5/4585* (2013.01); *A61F 2/70* (2013.01); *A61F 2/72* (2013.01); *A61F 5/01* (2013.01); *A61H 1/024* (2013.01); *A61H 1/0237* (2013.01); *A61H 1/0244* (2013.01); *A61H 1/0255* (2013.01); *A61H 1/0262* (2013.01); *A61H 1/0266* (2013.01); *A61H 1/0277* (2013.01); *A61H 1/0281* (2013.01); *A61H 1/0288* (2013.01); *A61B 5/4519* (2013.01); *A61B 5/6828* (2013.01); *A61B 5/6891* (2013.01); *A61B 2505/05* (2013.01); *A61B 2505/09* (2013.01); *A61H 2003/007* (2013.01); *A61H 2201/0103* (2013.01); *A61H 2201/0173* (2013.01); *A61H 2201/123* (2013.01); *A61H 2201/1215* (2013.01); *A61H 2201/149* (2013.01); *A61H 2201/1652* (2013.01); *A61H 2201/5007* (2013.01); *A61H 2201/5043* (2013.01); *A61H 2201/5064* (2013.01); *A61H 2201/5071* (2013.01); *A61H 2201/5092* (2013.01); *A61H 2230/105* (2013.01); *A61H 2230/605* (2013.01); *A61H 2230/625* (2013.01)

(58) Field of Classification Search
CPC ... A61B 5/4585; A61B 5/6828; A61B 5/6892; A61B 2505/05; A61B 2505/09; A61F 2/68; A61F 5/01; A61H 1/0237; A61H 1/024; A61H 1/0244; A61H 1/0255; A61H 1/0262; A61H 1/0266; A61H 1/0277; A61H 1/0281; A61H 1/0288; A61H 3/00; A61H 2003/007; A61H 2201/0103; A61H 2201/0173; A61H 2201/1215; A61H 2201/123; A61H 2201/149; A61H 2201/1652; A61H 2201/5007; A61H 2201/5043; A61H 2201/5064; A61H 2201/5071; A61H 2201/5092; A61H 2230/105; A61H 2230/605; A61H 2230/625

See application file for complete search history.

(56) References Cited

U.S. PATENT DOCUMENTS

| | | | |
|---|---|---|---|
| 5,845,540 A * | 12/1998 | Rosheim | B25J 3/04 74/490.05 |
| 5,901,581 A | 5/1999 | Jia-Wine et al. | |
| 6,301,526 B1 * | 10/2001 | Kim | B25J 9/0006 600/1 |
| 7,153,242 B2 | 12/2006 | Goffer | |
| 7,429,253 B2 * | 9/2008 | Shimada | A61F 5/0102 602/16 |
| 7,862,524 B2 * | 1/2011 | Carignan | B25J 17/025 601/5 |
| 8,070,700 B2 * | 12/2011 | Kazerooni | A61H 3/00 602/16 |
| 8,096,965 B2 | 1/2012 | Goffer et al. | |
| 8,170,287 B2 | 5/2012 | Dariush et al. | |
| 8,348,875 B2 | 1/2013 | Goffer et al. | |
| 8,396,595 B2 | 3/2013 | Dariush | |
| 8,801,639 B2 * | 8/2014 | Malosio | A61H 1/0274 601/33 |
| 8,905,955 B2 | 12/2014 | Goffer et al. | |
| 9,526,668 B2 | 12/2016 | Goffer et al. | |
| 9,566,705 B2 | 2/2017 | Goldfarb et al. | |
| 9,682,006 B2 | 6/2017 | Goldfarb et al. | |
| 9,693,926 B2 | 7/2017 | Goldfarb et al. | |
| 9,757,254 B2 | 9/2017 | Nagarajan et al. | |
| 9,782,322 B2 | 10/2017 | Nagarajan et al. | |
| 10,154,937 B2 | 12/2018 | Angold et al. | |
| 10,159,620 B2 | 12/2018 | Sandler et al. | |
| 10,195,736 B2 | 2/2019 | Barnes | |
| 10,226,395 B2 | 3/2019 | Goffer et al. | |
| 10,449,105 B2 * | 10/2019 | Hollander | A61F 2/68 |
| 2008/0009771 A1 * | 1/2008 | Perry | B25J 9/0006 600/587 |
| 2011/0040216 A1 * | 2/2011 | Herr | A61F 5/0102 601/34 |
| 2012/0010749 A1 * | 1/2012 | van der Merwe | A61F 2/586 700/264 |
| 2012/0172770 A1 | 7/2012 | Almesfer et al. | |
| 2014/0005577 A1 | 1/2014 | Goffer | |
| 2014/0100493 A1 * | 4/2014 | Craig | A61H 3/00 601/35 |
| 2014/0213951 A1 * | 7/2014 | Pietrusisnki | A61H 3/008 602/23 |
| 2015/0351995 A1 | 12/2015 | Zoss et al. | |
| 2016/0016309 A1 | 1/2016 | Swift et al. | |
| 2016/0045386 A1 | 2/2016 | Sandler et al. | |
| 2016/0067137 A1 | 3/2016 | Little et al. | |
| 2016/0235616 A1 | 8/2016 | Goffer et al. | |
| 2016/0250094 A1 | 9/2016 | Amundson et al. | |
| 2016/0270997 A1 | 9/2016 | Little et al. | |
| 2017/0246740 A1 | 8/2017 | Barnes | |
| 2017/0281453 A1 | 10/2017 | Goldfarb et al. | |
| 2017/0340504 A1 | 11/2017 | Sanz Merodio et al. | |
| 2018/0092536 A1 | 4/2018 | Sandler et al. | |
| 2018/0116828 A1 | 5/2018 | Quinn et al. | |
| 2019/0001493 A1 | 1/2019 | Hyun et al. | |

* cited by examiner

SYSTEM AND DEVICE FOR GUIDING AND DETECTING MOTIONS OF 3-DOF ROTATIONAL TARGET JOINT

FIELD OF INVENTION

This invention relates generally to spatial orientation guidance systems and more particularly to a system with motion generation, motion transfer, target interfacing, feedback, and controller subsystems that interact to actively guide or measure three degree-of-freedom rotational movements of joints or joint systems capable of three degree-of-freedom rotational movements.

BACKGROUND OF INVENTION

Unless otherwise indicated herein, the materials described in this section are not prior art to the claims in this application and are not admitted to be prior art by inclusion in this section.

With respect to exoskeleton applications, an estimated 20,639,200 (7.1%) of non-institutionalized United States residents suffered from an ambulatory disability in 2013, while an approximated 2,512,800 (7.2%) of Canadians reported mobility disablements in 2012. These disabilities cost an estimated annual equivalent of $375 billion in family caregiver support, in addition to significant economic and social burdens to the patient and the healthcare system.

One emergent technology that aims to diminish this health problem and improve the quality of life for sufferers is the lower-body exoskeleton: wearable robotic systems that completely or partially support their user's weight and provide controlled guidance of leg movements, thereby allowing their user to stand and walk. This solution provides benefits over wheelchair use and other traditional means because it can also help reduce secondary complications of immobility such as pneumonia, blood clots, pressure sores, and lowered self-esteem. However, one major shortcoming of current exoskeleton technologies is a limited range of motion about the hip and ankle joints, which are both capable of three rotational degrees-of-freedom (DOFs) in the human body. In general, current technologies actively guide one degree-of-freedom hip-centered movements with absent or only passive allowance for one or both of the other DOFs. This design scheme generally results in a serial joint structure within the exoskeleton device, which has an inherently lower payload-to-weight ratio than a parallel structure counterpart. Therefore, this characteristic leads to bulkier than necessary devices.

Furthermore, the instability that arises from kinematic restrictions on human joint capabilities often requires attendant use of walking sticks to maintain bodily balance while standing or moving. So, in order to safely operate the exoskeleton system, a user must coordinate motions with additional equipment using their upper body. The inconvenience and effort associated with this requirement causes fewer potential users from adopting the technology and altogether prevents other people from operating the devices who could otherwise benefit from the technology if not for this requirement.

SUMMARY OF THE INVENTION

In one aspect, a device for guiding and detecting motions of a target joint is provided. The device comprises a motion generator configured to generate a three degree-of-freedom (3-DOF) motion of the target joint, a motion transfer and target interfacing unit configured to convert the motion generated by the motion generator to the target joint so that the target joint moves with a 3-DOF about its own center of rotation, and a controller that is in communication with the motion generator and the motion transfer and target interfacing unit to control the motion generator and the motion transfer and target interfacing unit. The motion generator comprises a plurality of actuators and a network of joints and linkages to mechanically interconnect the plurality of actuators and connect the motion generator to one end of the motion transfer and target interfacing unit. The coordinated movements of the actuators, joints, and linkages provide the 3-DOF rotational motion of the target joint. The motion transfer and target interfacing unit comprises at least one rotary joint, at least one linear-motion joint and a network of linkages interconnecting the least one rotary joint and the at least one linear-motion joint and connecting the motion transfer and target interfacing unit to the motion generator and the target joint. The controller comprises an input unit, an output unit and a processing unit, and is configured to send output signals to the motion generator and/or motion transfer and target interfacing unit to control the driver of the plurality of actuators.

The motion guiding device further comprises a motion detection and feedback unit in communication with the motion generator and the controller. The motion detection and feedback unit comprises a plurality of sensors to detect a position and/or an orientation of the actuators of the motion generator and/or motion transfer and target interfacing unit, and a position and/or an orientation of the target joint. The motion detection and feedback unit further feeds the detected signals to the controller.

In one aspect, the target is a human hip joint. The device further comprises a means to mount and secure the motion guiding device to a user. The mounting means comprise one or more adjustable straps and one or more orthotics.

In one aspect, the motion guiding device is a human joint exoskeleton.

In another aspect, the target joint is a ball-and-socket joint and the motion guiding device is a camera positioning device or a propeller orientation control device.

In another aspect, the target joint is a 3-DOF joint and the motion guiding and detecting device is remote motion generation and guiding device.

In one aspect, a motion assistance system is provided. The system comprises a first motion guiding and detecting device for guiding motion of a first target, at least one additional motion guiding and detecting device for guiding motion of another target, a controller in communication with the first motion guiding and detecting device and the at least one additional motion guiding and detecting device to coordinate motions of the multiple targets and a means to mount and secure the motion assistance system to a user such that the motion assistance system supports a weight of the user.

In one aspect, a motion capture and force feedback system is provided. The system comprises a first motion guiding and detecting device for detecting and guiding motion of a first target joint, at least one additional motion guiding device for detecting and guiding motion of another target joint, a plurality of sensors connected to the first and the at least one additional motion guiding and detecting devices where the plurality of sensors are configured to detect motions of the first motion guiding and detecting device and the at least one additional motion guiding and detecting device. The system further comprises a controller in communication with the plurality of sensors to receive detected signals from the plurality of sensors and calculate a position and an orientation of each target joints.

In another aspect, the controller of the motion capture and force feedback system is pre-programmed to control each of the motion guiding and detecting devices to resist motions of the motion guiding and detecting devices in certain directions/orientations or to apply forces to the target joint in certain directions/orientations.

In addition to the aspects and embodiments described above, further aspects and embodiments will become apparent by reference to the drawings and study of the following detailed description.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure. Sizes and relative positions of elements in the drawings are not necessarily drawn to scale. For example, the shapes of various elements and angles are not drawn to scale, and some of these elements are arbitrarily enlarged and positioned to improve drawing legibility.

DETAILED DESCRIPTION OF SPECIFIC EMBODIMENTS

This invention provides decoupled or combined positioning for all three rotational degrees-of-freedom of a ball-and-socket joint or a quasi ball-and-socket joint without applying significant tensile or compressive forces to the targeted protrusion from such joint. One application can be a hip exoskeleton or any other human joint exoskeleton, for which the joint targeted for positioning is the human joint. Another possible application can be as part of a ball-and-socket-based camera positioning system.

Figure 1:
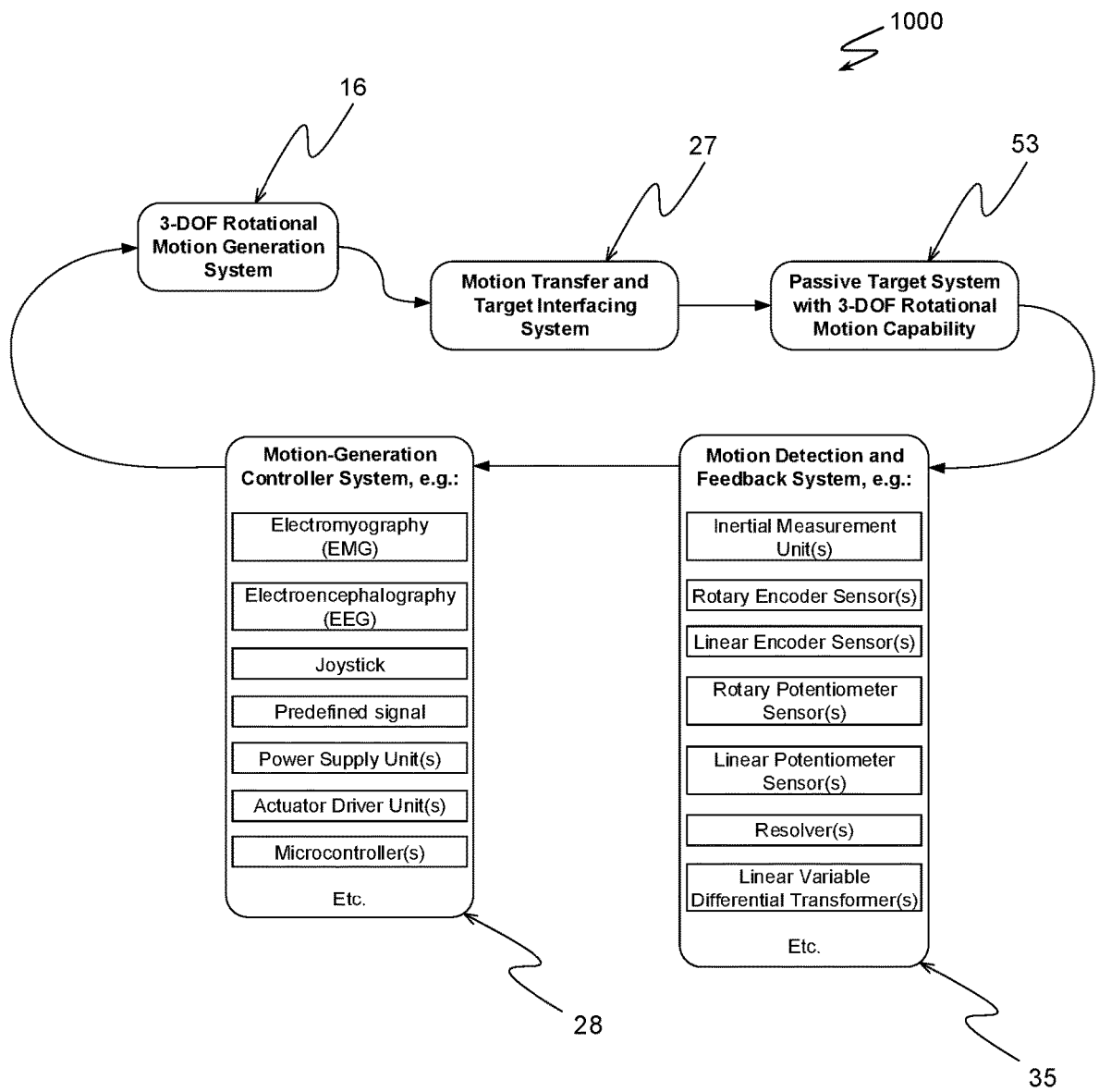
FIG. 1 is a flowchart of an example of a device for guiding motions of a target showing its subsystems and their interactions.

FIG. 1 illustrates a device 1000 for guiding motions of three degree-of-freedom (DOF) joint systems that comprises a 3-DOF motion generator 16, a motion transfer and target interfacing unit 27 and a target joint 53. The motion transfer and target interfacing unit 27 is configured to provide decoupled or combined 3-DOF rotational motion or inaction to the target joint 53. The target 53 may be any structure containing a 3-DOF rotational joint (e.g. passive ball-and-socket joint), or a quasi-3-DOF rotational joint (e.g. a hip joint of a mobility disabled person), or any other active target joint (e.g. hip joint able to have complete or partial mobility by human). The active target joint is defined as any target joint that has an ability to perform a 3-DOF rotational movement on its own without assistance of an external motion assistance device. For example, a human hip joint is an active joint since it can move on its own, however, in case when a person is incapable of producing motion (e.g. they are paralyzed) and the hip joint (or any other human joint) is only moved using a motion assistance device, then such human joint can be considered a passive target joint. So, in general, any joint capable of producing its own movement is considered active while a joint that is moved only using some structure (actuators) is considered passive joints. In practice, there might be a situation where a joint is capable to move (active), but with extra assistance it can be faster, longer, better, etc.

The motion generator 16 conveys mechanical action to the target joint 53 via the motion transfer and target interfacing unit 27, which physically supports the target 53 in some extent and converts action from the motion generator 16 to the desired movements of the target 53. The device 1000 further comprises a control unit 28 and a motion detection and feedback unit 35. The control unit 28 can comprise one or more input/output units and a processing unit. The input unit can comprise for example a joystick/keyboard, a touch screen, a voice recognition unit or any other user interface to input any command/instructions/parameters while an output unit can comprise an actuator driver unit to send trigger signals to, for example, the motion generator 16. The controller 28 can further comprise one or more microcontrollers, a power supply unit, a predefined signal processing unit for signal conditioning or signal filtering (e.g. filtering or calibrating signals obtained as an input), etc. For example, in one implementation, the control unit 28 can receive signals from an Electromyograph (EMG) and/or Electroencephalograph (EEG) as an input. The EMG is a device that is used to detect the electrical activity of the muscles and EEG is used to detect the electrical activity of the brain. The signals obtained from the EMG and/or EEG are processed by the processing unit of the controller 28 to determine the desired motion of the target joint 53 and then trigger signals are sent to the motion generator 16 to generate such motion. The EMG and EEG can be, for example, part of the motion detection and feedback unit 35. The motion detection and feedback unit 35 can further comprise at least one of an inertial measurement unit, a rotary encoder sensor, a linear encoder sensor, a rotary potentiometer sensor, a linear potentiometer sensor, a resolver, a linear variable differential transformer, to detect a position and an orientation of the target 53 and/or a position and an orientation of each actuators 5-7 (see FIG. 2) of the motion generator 16 and feed such signals as an input to the controller 28.

Figure 2:
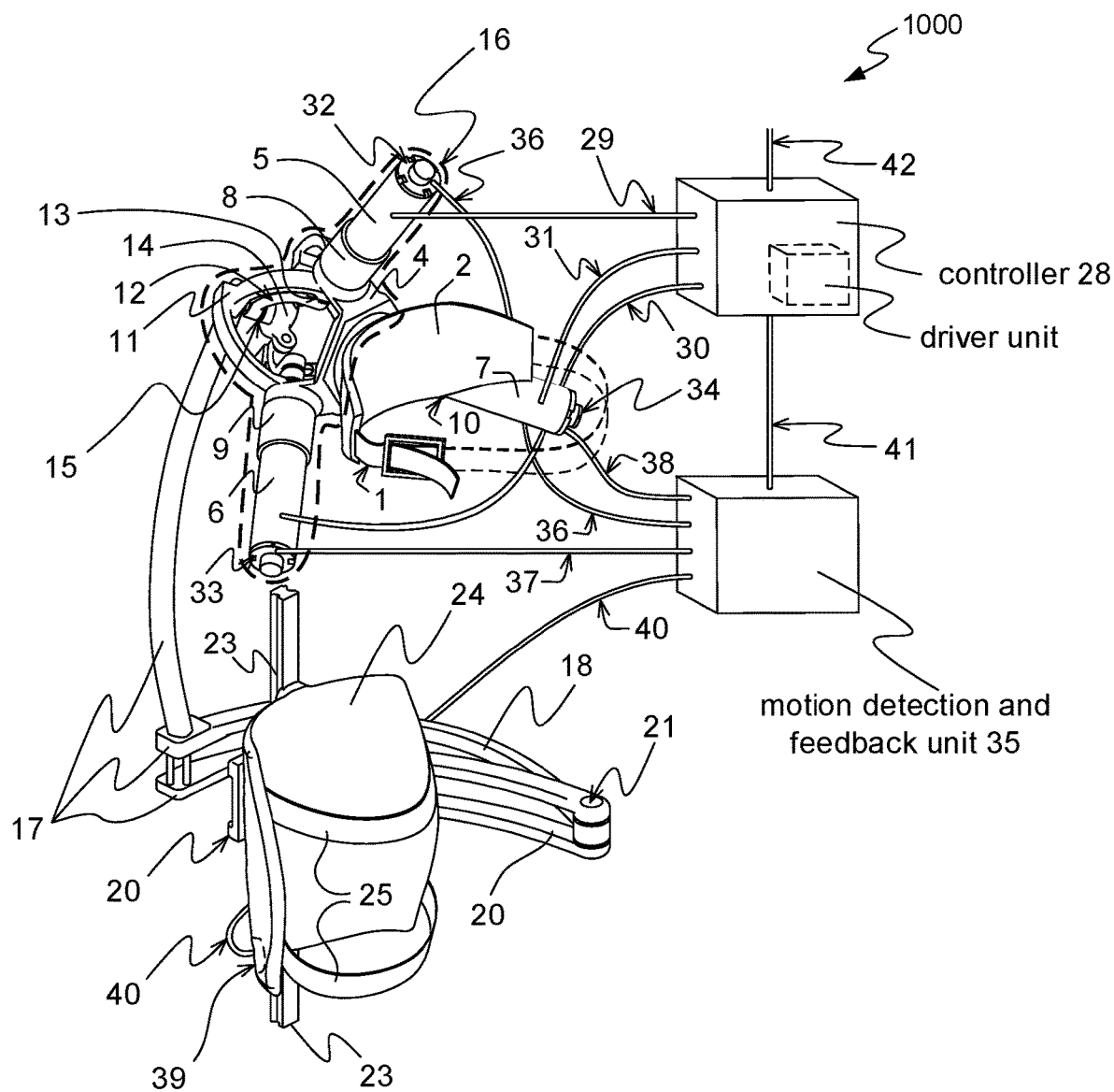
FIG. 2 is a side view of an example of a device for guiding motions of a passive 3-DOF joint system used as a hip joint exoskeleton module showing its components and subcomponents connections.

FIG. 2 illustrates the device 1000 for guiding and detecting motions of a three degree-of-freedom (DOF) joint system of the present invention used as a hip joint exoskeleton module. An ergonomic adjustable-length strap 1 and a trunk orthotic 2 can be used to attach the device 1000 to the human body, for example adjacent to the hip joint, so that the device 1000 can be easily mounted for use or taken off when not in use. This is for illustrational purposes only and person skilled in the art would understand that the device 1000 can be used for guiding and detecting motions of any other human target joint (i.e. a knee, an ankle, a shoulder, a wrist, an elbow, a finger, etc.) or any other target joint (i.e. a ball-and-socket spherical joint) without departing from the scope of the invention.

Attached to the trunk orthotic 2 is the 3-DOF rotational motion generator 16 that can comprise an actuator base structure 4 which can rigidly support three rotary actuators 5-7. The actuators 5-7 can interface with corresponding gearheads 8-10. The gearheads 8-10 are alternative and, in some implementations, they can be omitted. Each gearhead 8-10 or rotary actuator 5-7, if the former is absent, connects to a distal linkage 11. Sequentially, each distal linkage 11 connects to a proximal linkage 12 via a passive 1-DOF rotary joint 13. Each proximal linkage 12 in turn connects to a moving component, such as a moving plate 14, via another passive 1-DOF rotary joint 15.

Moving plate 14 is attached to a linkage 17, which connects to another linkage 18 by way of a passive 1-DOF rotary joint 19. Sequentially, the aforementioned linkage 18 connects to yet another linkage 20 via another passive 1-DOF rotary joint 21. This final linkage 20 is attached to a sliding component 22 (see FIG. 3) of a linear-motion joint. The linear-motion joint can be for example a passive 1-DOF prismatic joint, a 2-DOF cylindrical joint or a linear motor, in which the sliding component 22 is configured to slide up and down along a corresponding track component 23. The track component 23 is connected to an ergonomic upper leg orthotic structure 24 with attached straps 25 that facilitate interface with the user's upper leg 26 (see FIG. 3). With respect to this embodiment of the device 1000, the components 1, 2, 17-25 are part of the motion transfer and target interfacing unit 27 while components 4-15 are part of the motion generator 16. Person skilled in the art would understand that any of the passive rotary or prismatic joints of the motion generator 16 and/or the motion transfer and target interfacing unit 27 can be replaced with an active rotary/linear joints, such as for example rotary/linear actuators, without departing from the scope of the invention.

Generally, for supporting the 3-DOF motion required by target joint 53, the motion generator 16 and the motion transfer and target interfacing unit 27 collectively can contain at least three actuators. For example, in a 2-DOF agile eye type of joint, the motion generator 16 can comprise two actuators while the motion transfer and target interfacing unit 27 can comprise one actuator. The number of the actuators can be reduced or replaced by passive rotary or prismatic joints according to the number of the DOFs of the target 53 that doesn't require actuation. Any and all actuators of the motion generator 16 and/or the motion transfer and target interfacing unit 27 can be selected from an electric motor, a pneumatic motor, a hydraulic motor or any other motor or combination thereof. In one implementation, the actuators can be located remotely from the motion guiding and detecting device (e.g. in a backpack carried by the user) and can actuate the motion generation by a drive-by-wire. The purpose of the motion transfer and target interfacing unit 27 is to connect and transfer motions between the motion generator 16 and the target joint 53 or to contribute to the motion guiding device's actuation if an actuator is included in the motion transfer unit 27.

The controller 28 is in communication with the motion generator 16 and can trigger such motion generator 16 to achieve a desired action or inaction of the target joint 53. This controller 28 can include a software execution commanding to trigger the actuators 5-7 via an appropriate driver subsystem. Additionally, the controller 28 can be programmed to receive control signals from the electromyograph, electroencephalograph, or the instructions can be inputted directly via joystick, keyboard or other input unit, or the controller's software may be executed based on a predefined routine pre-programmed therein. Furthermore, the controller 28 can receive input information from the motion detection and feedback unit 35 that interfaces with and monitors the target 53 and the actuators 5-7. The motion detection and feedback unit 35 may acquire information on the target joint's state using one or more inertial measurement units, rotary encoder sensors, linear encoder sensors, rotary potentiometer sensors, linear potentiometer sensors, resolvers, linear variable differential transformers, foot force sensors, etc. or a combination of the above. In one implementation, sensors of the motion detection and feedback unit 35 can interface with and monitor the position and/or orientation of the actuators 5-7. In one implementation, the sensors of the motion detection and feedback unit 35 may detect the position and/or the orientation of the target joint 53, in applications such as to identifying user's intention and/or to electronically store sensor readings for later transfer to a computer (controller) to collect error information and/or motion capture data.

As shown in FIG. 2, rotary actuators 5-7 receive control signals from the controller 28 via connections 29-31 respectively. Furthermore, sensors 32-34 are respectively attached to the rotary actuators 5-7 to provide information to the motion detection and feedback unit 35 via connections 36-38. Additionally, a sensor package 39 provides data to the motion detection and feedback unit 35 via connection 40. The motion detection and feedback unit 35 provides information to the controller 28 via connection 41. When applicable, the controller 28 receives and/or sends data to a similar controller of another device 1000 for coordinating movements (e.g. two exoskeleton units could coordinate gait movements) via connection 42. All of the above connections 29-31,36-38, and 40-42 may be wired or wireless.

Figure 3:
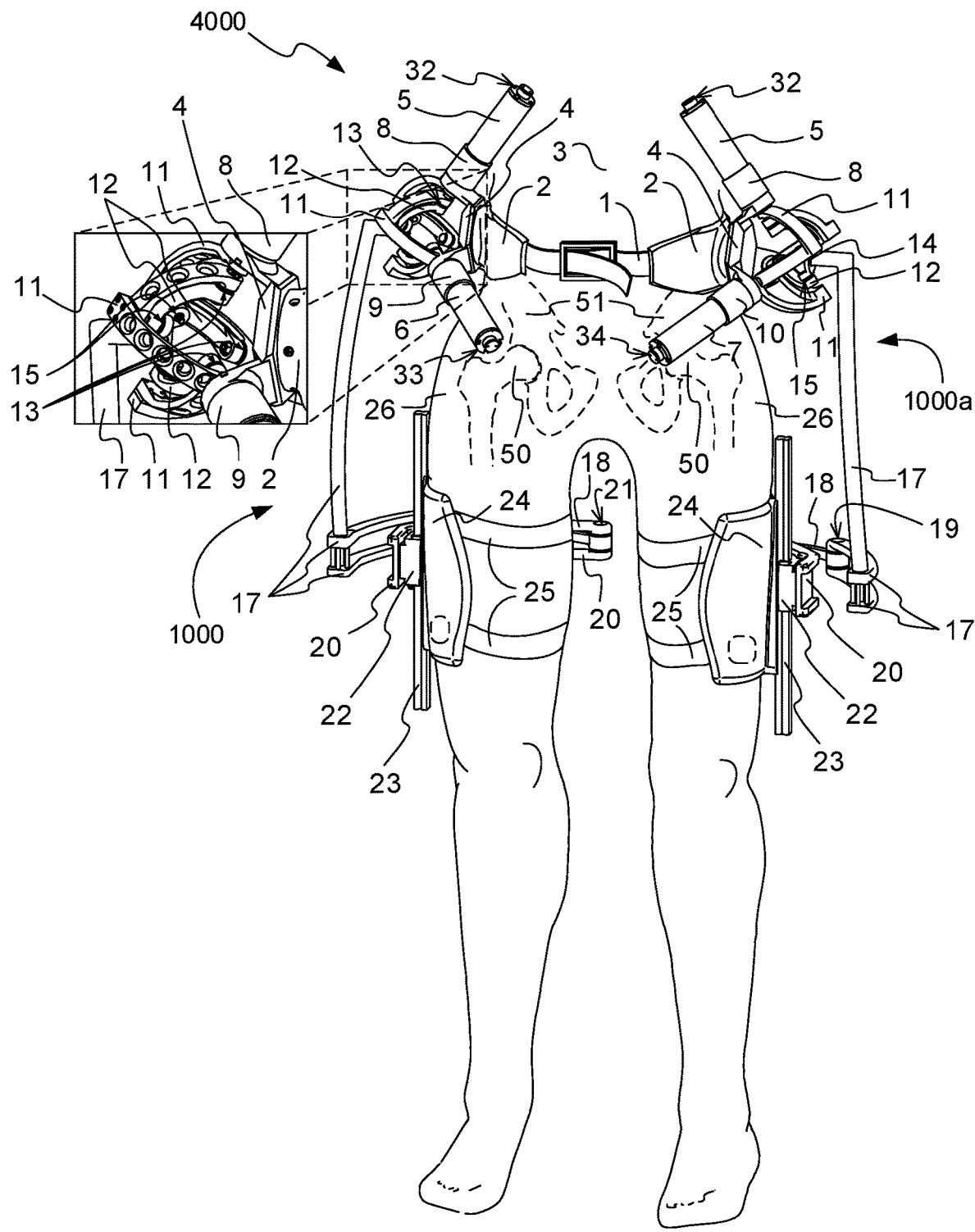
FIG. 3 is a front view an example of a motion assistance system used as an exoskeleton system showing two devices for guiding motions of passive 3-DOF joint systems mounted on each side of a human user.
Figure 4:
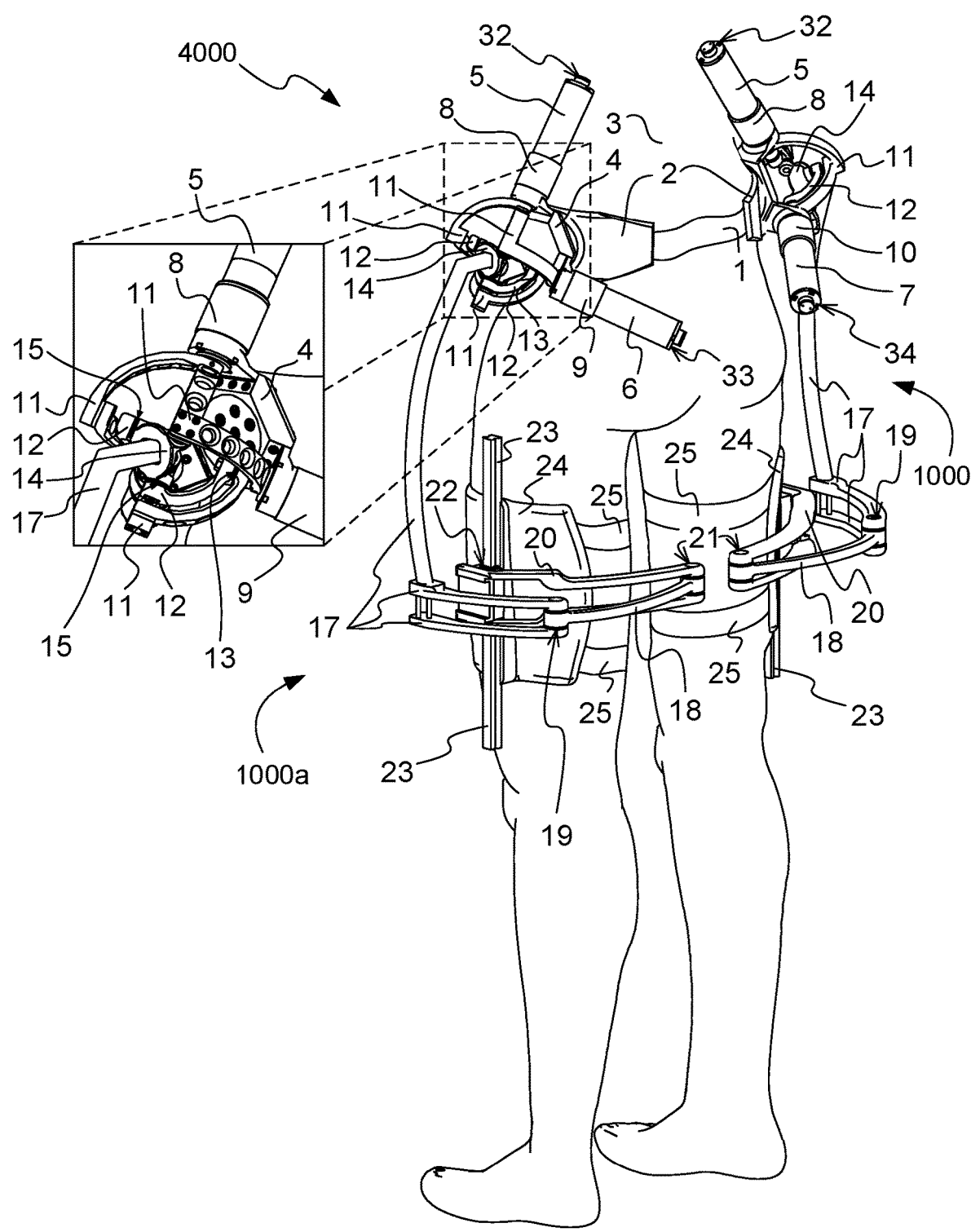
FIG. 4 is a back view of the motion assistance system shown in FIG. 3.

FIGS. 3 and 4 show a motion assistance system 4000 mounted to a user 3. The motion assistance system 4000 can comprise two of the motion guiding and detecting devices 1000, 1000a that are mounted on each side of the user 3 (e.g. one per each hip of the user 3). The controller 28 of one of the devices 1000 is in communication with a controller of the other device 1000a to synchronize and coordinate their movements. The two controllers can identify user's intention based on the information obtained from the respective sensors of the corresponding motion detection and feedback units and can then send the appropriate triggering signal to the drivers of the actuators of the respective motion generation units to generate specific motion. In one implementation, the controller 28 of the first motion guiding and detecting device 1000 can be in communication with the motion generator and the motion detection and feedback unit of the second device 1000a such that a single controller 28 can control the movement of the both motion guiding and detecting devices 1000, 1000a.

Figure 5:
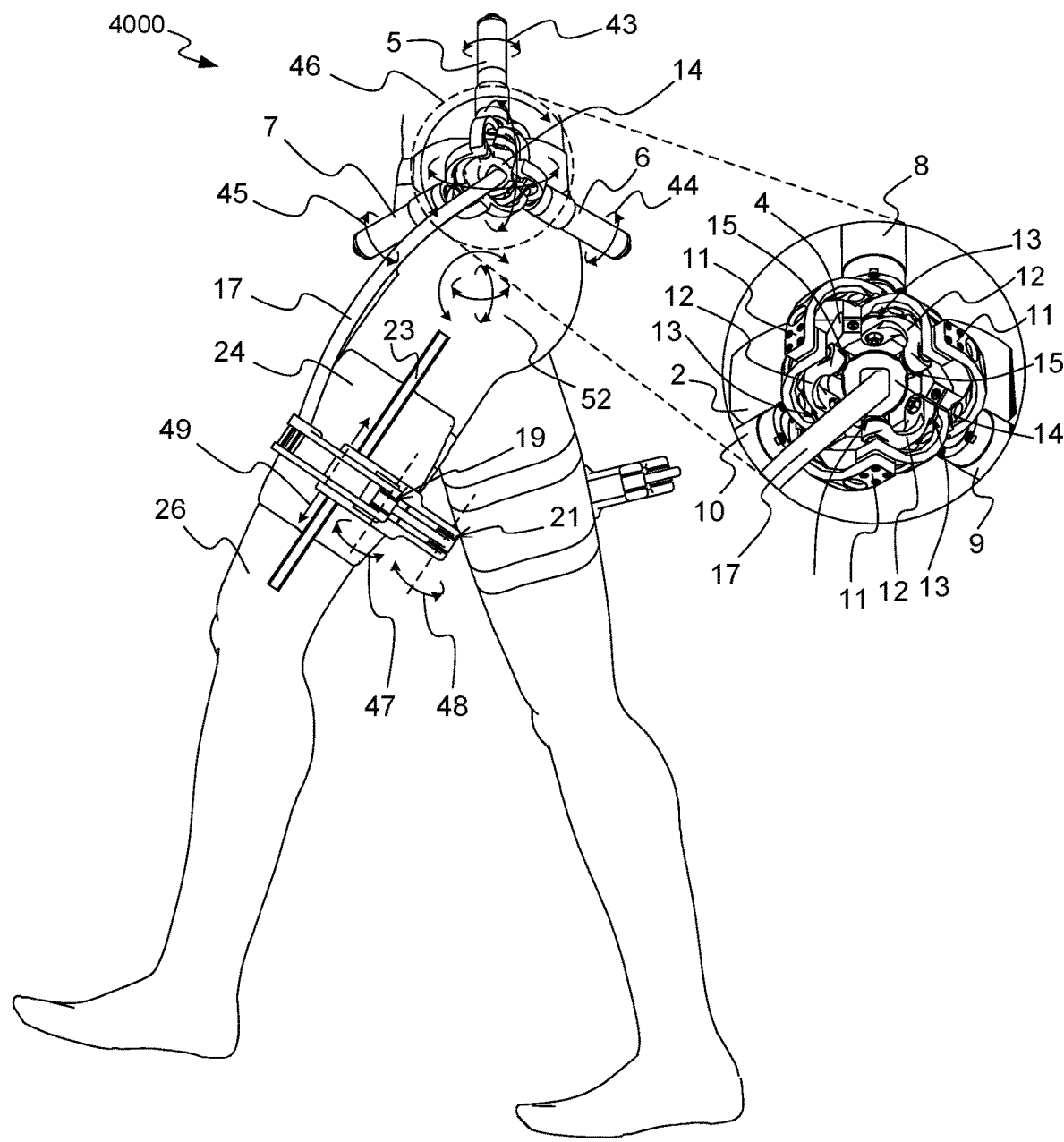
FIG. 5 is a side view of an example of a motion assistance system used as an exoskeleton system mounted to a human user.
Figure 6:
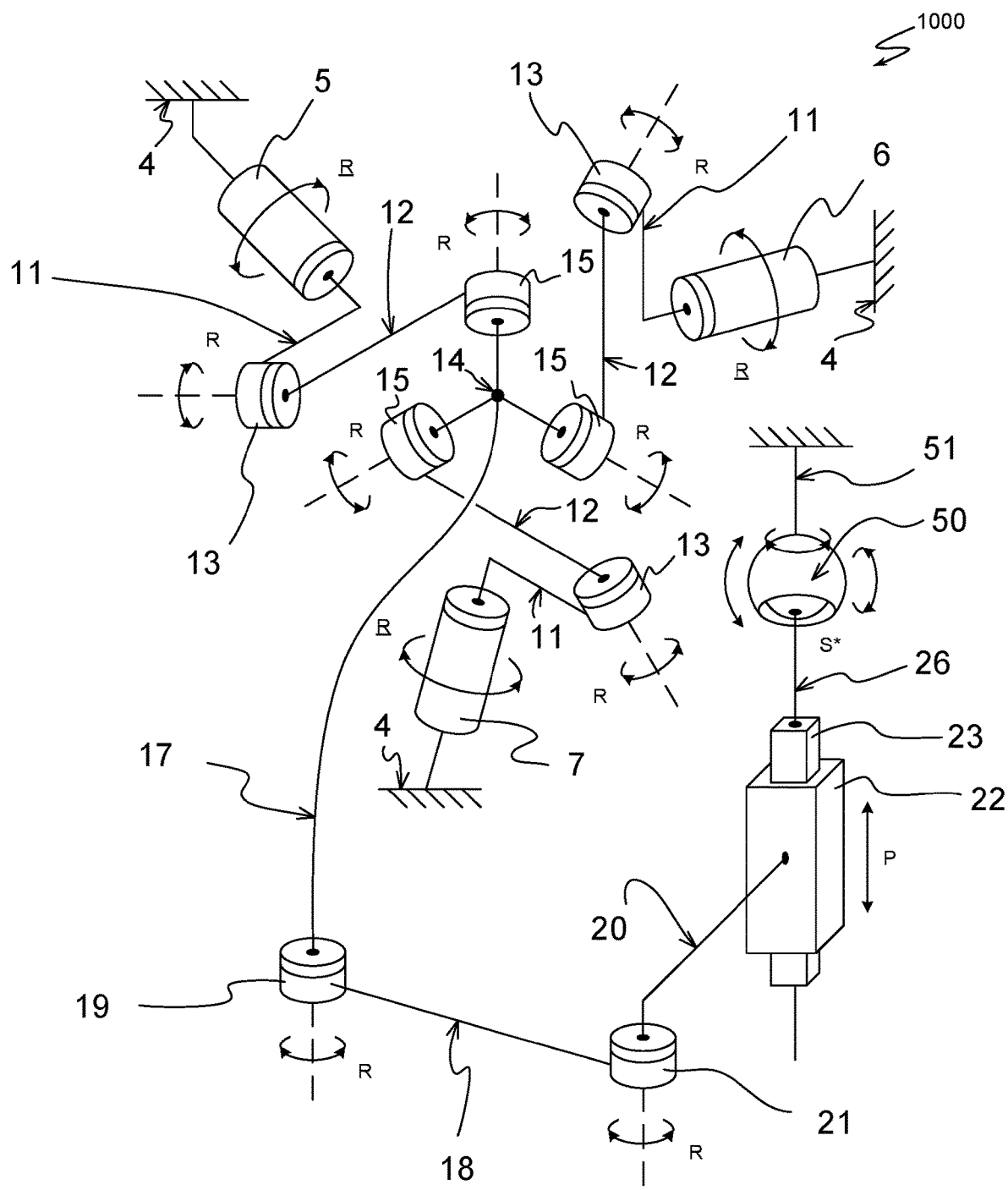
FIG. 6 is a mechanical schematic of an example of a device for guiding motions of a target showing joint and linkage components with joint motion capabilities where as labeled 'R' designates rotary joints, 'P' designates prismatic joints, 'S' designates ball-in-socket joints, underline designates active joints, no underline designates passive joints, and '*' designates the target joint for guidance.

FIG. 5 illustrates a motion assistance exoskeleton system 4000 used as an aid device to help the user during walking operation. As depicted in FIG. 5, the respective coordinated actions 43-45 of the rotary actuators 5-7 generate 3-DOF rotary motion 46 of the moving plate 14 about its center of rotation point that does not coincide with the center of rotation of the hip joint. The linkage 17 also experiences a 3-DOF rotary motion about that point because it is attached to the moving plate 14. Motion of the linkage 17 produces synchronized responses 47 and 48 of the passive rotary joints 19 and 21 along with the response 49 of the passive prismatic joint resulting in an interaction between the sliding component 22 and the track component 23. FIG. 6 more clearly illustrates the correlation between actions of the actuators 5-7 and corresponding motion and actions of the respective linkages and passive joints. The combination of the above motions 43-49 result in a motion response by the target joint, such as the user's hip joint 50 (i.e. upper leg's motion with respect to the pelvis 51) in one or any combination of its 3-DOF rotation capabilities 52 when the exoskeleton system is properly interfaced with the human body via the motion transfer and target interfacing unit 27. The system of linkages 17,18 and 20, and the passive rotary and prismatic joins 19,21 and the sliding component 22, interconnected as described above provide 3-DOF motion with a center of rotation that coincide with the center of rotation of the hip joint, despite the fact that the center of rotation of the moving plate 14 of the motion generation unit 16 does not overlap with the center of rotation of the hip target joint 50. Thus, the motion generation unit 16 can be mounted away from the hip and the motion transfer and target interfacing unit 27 will allow 3-DOF motion of the hip target joint 50 about the center of rotation of such target 50 (or an arbitrary point in space). The motions 43-49 and the user's hip joint response are all facilitated by the collective DOFs of the passive (or in some implementations active) rotary and/or prismatic joints.

The target joint 53 in FIGS. 3-5 corresponds to the hip joint 50, between the user's upper leg 26 and pelvis 51. As described herein above, the target 53 is considered passive as long as the user does not provide sufficient exertion on the hip joint to cause motion about it or hold it in place when subject to external torques. For example, if rotary actuators 5-7 each hold their angular position constant, the rest of the system and the user's hip joint will also cease motion and retain the positional states of the moment (i.e. aside from any minor transient responses). Furthermore, with regard to any interfaced protrusion from the target joint 53, the motion transfer and target interfacing unit 27 prevents or minimizes forces along the protrusion's axis passing through the target joint 53, thereby reducing the risk of damage to the target joint 53.

Figure 7:
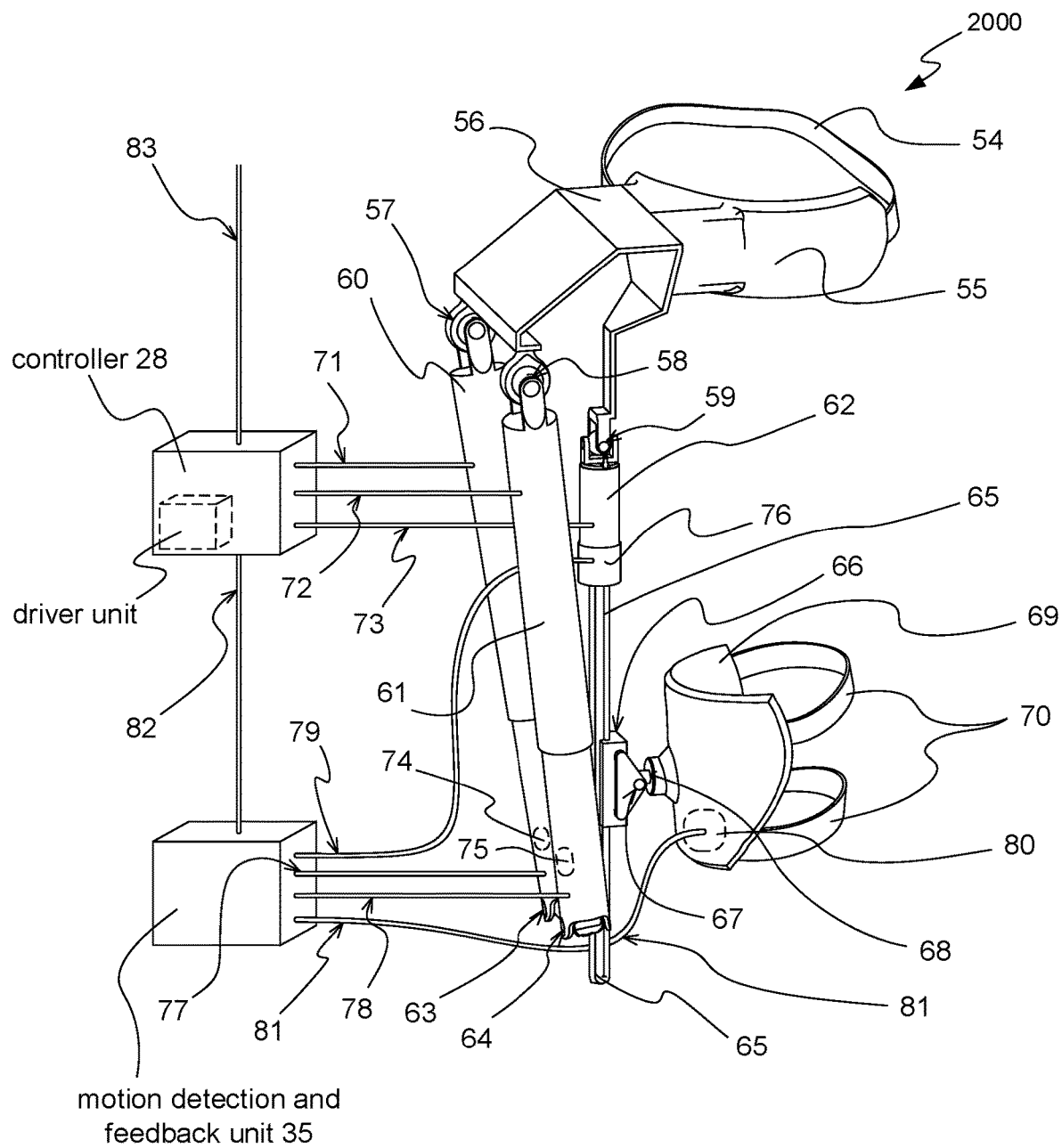
FIG. 7 is a side view of another embodiment of a device for guiding motions of passive 3-DOF joint system used as a hip joint exoskeleton module showing its components and subsystem connections.

FIG. 7 depicts another embodiment of a device 2000 for guiding and detecting motions of a 3-DOF joint system of the present invention. The device 2000 can also be used as a hip exoskeleton joint. An ergonomic adjustable-length strap 54 and a trunk orthotic 55 can be attached to the human body superior to the hip joint (i.e. at the user's trunk 3) in preparation for to device to be used or easily taken off when not in use. Attached to the trunk orthotic 55 is a base structure 56, which rigidly supports two passive spherical joints 57-58 and one passive universal joint 59. The spherical joints 57-58 may alternatively consist of three passive 1-DOF rotary joints, while the universal joint 59 may alternatively consist of two passive 1-DOF rotary joints. Both of the spherical joints 57-58 connect the base structure 56 to separate linear actuators 60-61, while the universal joint 59 connects the base structure 56 to a rotary actuator 62. These actuators may or may not interface with corresponding gearheads 74-76. The actuated bodies of the linear actuators 60-61 connect to corresponding universal joints 63-64, each of which may alternatively be realized as two passive 1-DOF rotary joints. Sequentially, both universal joints 63-64 attach to a single track component 65. Additionally, the gearhead or the rotary actuator 62, if the former is absent, connects to the same track component 65 at a different point such that the rotary actuator's axis of rotation is parallel to the longitudinal axis of the track component 65. With respect to this specific embodiment, components 56-64 comprise the 3-DOF rotational motion generation unit 16.

A sliding component 66 interacts with the track component 65 to create a linear-motion (i.e. a prismatic or a cylindrical) joint. In turn, the sliding component 66 connects to a passive 1-DOF rotary joint 67 which connects to another non-parallel and passive 1-DOF rotary joint 68. Sequentially, the 1-DOF rotary joint 68 attaches to an ergonomic upper leg orthotic structure 69 with straps 70 that facilitate interface with the user's upper leg 26. For this embodiment, the components 54, 55, and 65-70 are part of the motion transfer and target interfacing unit 27. The passive rotary or linear joints of the motion generator 16 and/or the motion transfer and target interfacing unit 27 can be replaced with an active rotary/linear joints, such as for example rotary/linear actuators, without departing from the scope of the invention As shown in FIG. 7, the linear actuators 60-61 and the rotary actuator 62 receive signals from the controller 28 via connections 71-73 respectively. Furthermore, sensors 74-76 are respectively attached to the actuators 60-62 and provide information to the motion detection and feedback unit 35 via connections 77-79. Additionally, a sensor package 80 provides data to the motion detection and feedback unit 35 via connection 81. The motion detection and feedback unit 35 provides information to the controller 28 via connection 82. When applicable, the controller 28 receives and/or sends data to a controller of another device 2000 for coordinating movements (e.g. two devices could coordinate gait movements) via connection 83. All of the above connections 71-73, 77-79, and 81-83 may be wired or wireless.

Figure 8:
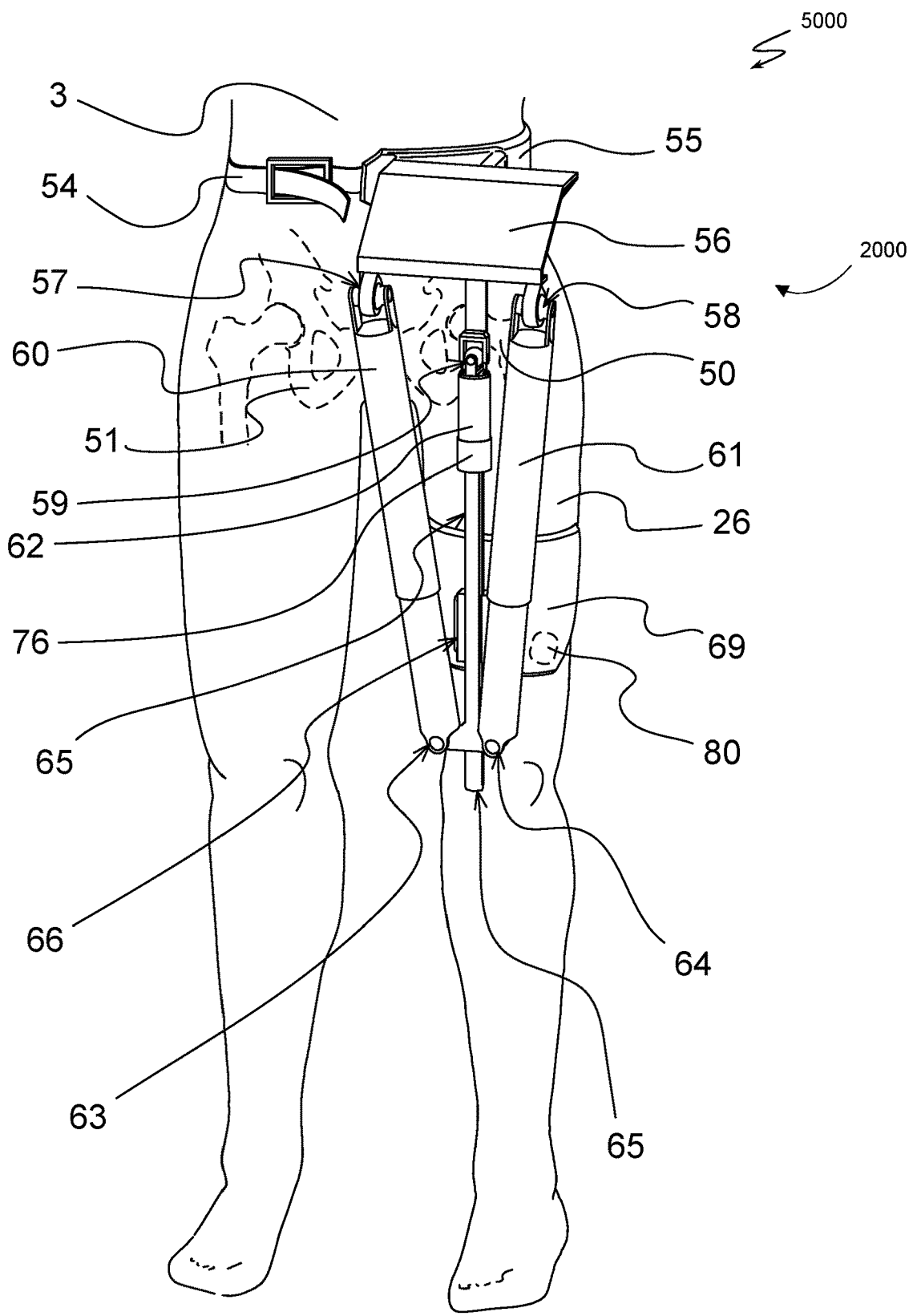
FIG. 8 is a front view an example of a motion assistance system comprising two of motion guiding devices of FIG. 7.
Figure 9:
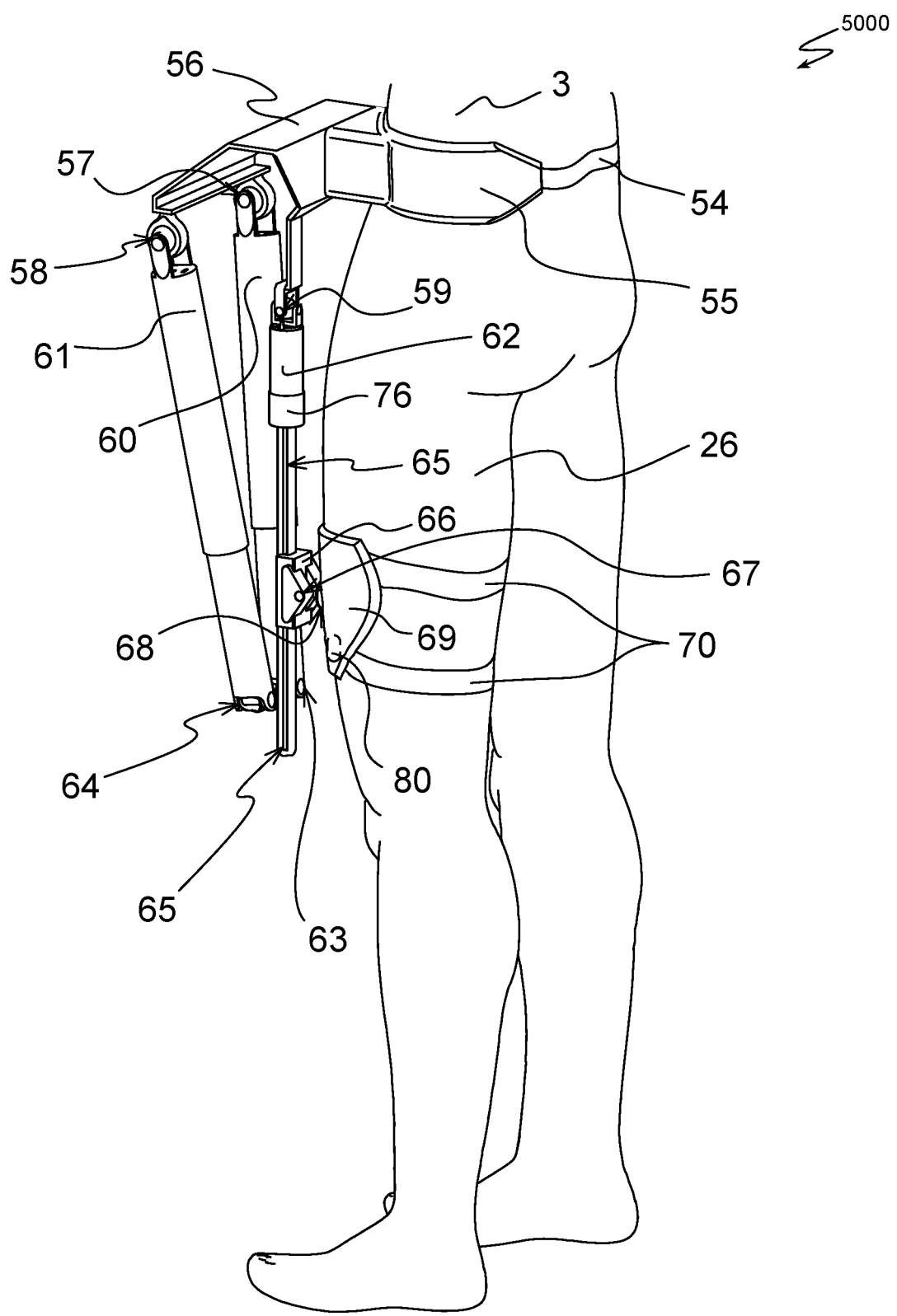
FIG. 9 is a back view of the motion assistance system of FIG. 8 mounted to a human user.
Figure 10:
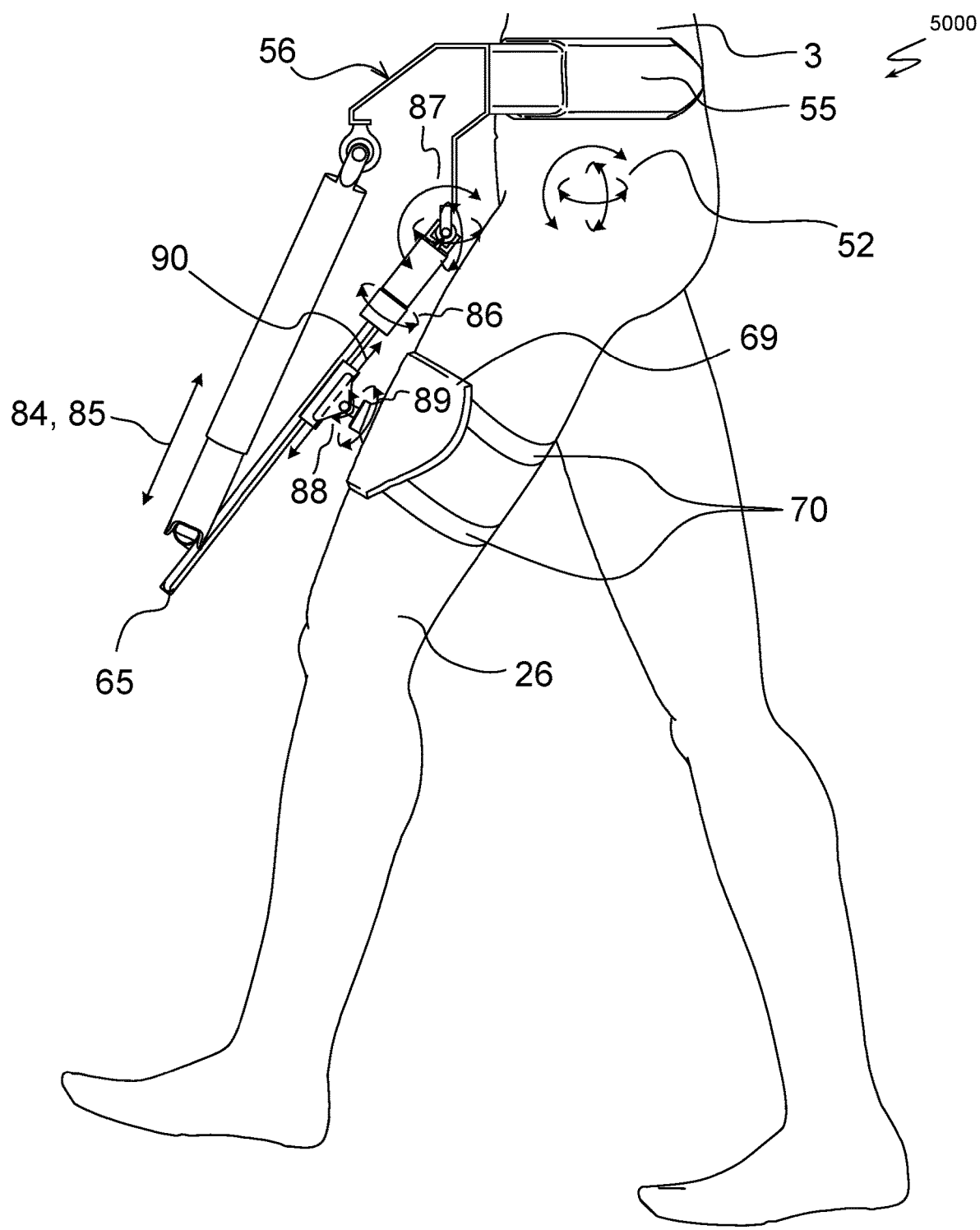
FIG. 10 is a side view of an example of a motion assistance system mounted to a human user.
Figure 11:
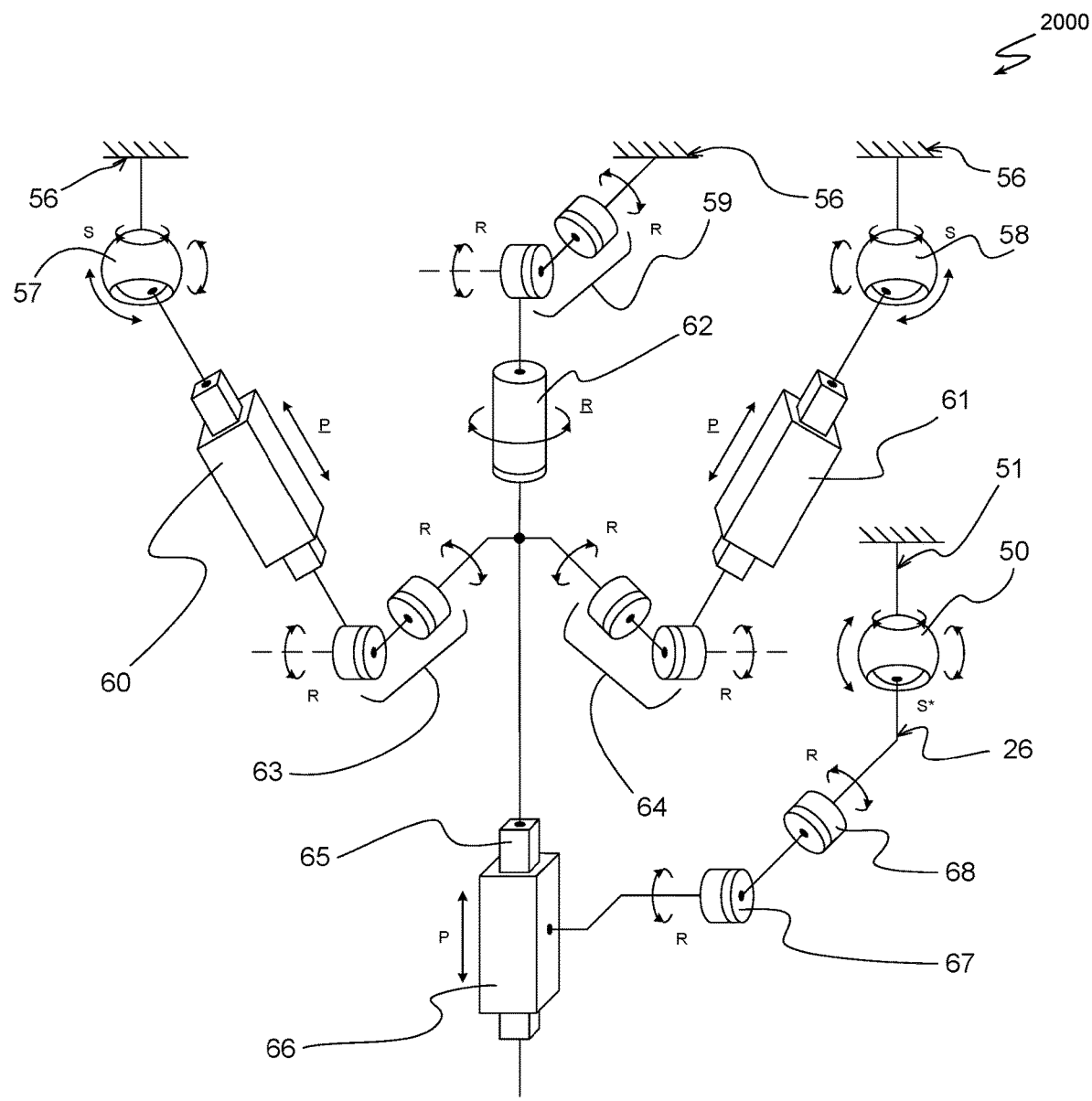
FIG. 11 is a mechanical schematic of an example of a device for guiding motions of a target showing joint and linkage components with joint motion capabilities where as labeled 'R' designates rotary joints, 'P' designates prismatic joints, 'S' designates ball-in-socket joints, underline designates active joints, no underline designates passive joints, and '*' designates the target joint for guidance.

FIGS. 8, 9 and 10 show a motion assistance system 5000 that comprises two of the motion guiding and detecting devices 2000 mounted on each side of a user 3. FIGS. 8-10 show only one motion guiding and detecting device 2000 but person skilled in the art would understand that the motion assistance system 5000 can comprise two such devices 2000 mounted on each side of the user 3 (one device per side). In some implementations (see FIGS. 21-23), the motion assistance system can comprise two or more guiding and detecting devices connected in series and mounted at one side of the user to guide the motions of different target joints, e.g. hip, knee and ankle joints or any other human target joints (i.e. shoulder, wrist, elbow, finger joints, etc.). As depicted in FIG. 10, the coordinated actions 84-86 of the actuators 60-62 generate 3-DOF rotary motion 87 of the track component 65 about a center of rotation point coincident to the rotational center of the universal joint 59. Motion of the track 65 produces synchronized responses 88 and 89 of the passive rotary joints 67 and 68 along with the response 90 of the passive prismatic joint resulting from the interaction between the sliding component 66 and the track component 65. The combination of the above motions 84-90 result in a motion response by the user's hip joint 50 (i.e. upper leg 26 motion with respect to the pelvis 51) in one or any combination of its 3-DOF rotation capabilities 52 when the exoskeleton device is properly interfaced with the human body via the motion transfer and target interfacing unit 27. The motions 84-90 and the user's hip joint response are all facilitated by the collective DOFs of the embodiment's passive joints. In another aspect, if the actuators 60-62 each hold their angular position constant, the rest of the system and the user's hip joint will also cease motion and will retain the positional states of the moment (i.e. aside from any minor transient responses). The target 53 is considered passive as long as the user does not provide sufficient exertion on the hip joint to cause motion about it or hold it in place when subjected to external torques. FIG. 11 more clearly illustrates the correlation between actions of the actuators and the corresponding motion and actions 84-90.

Figure 12:
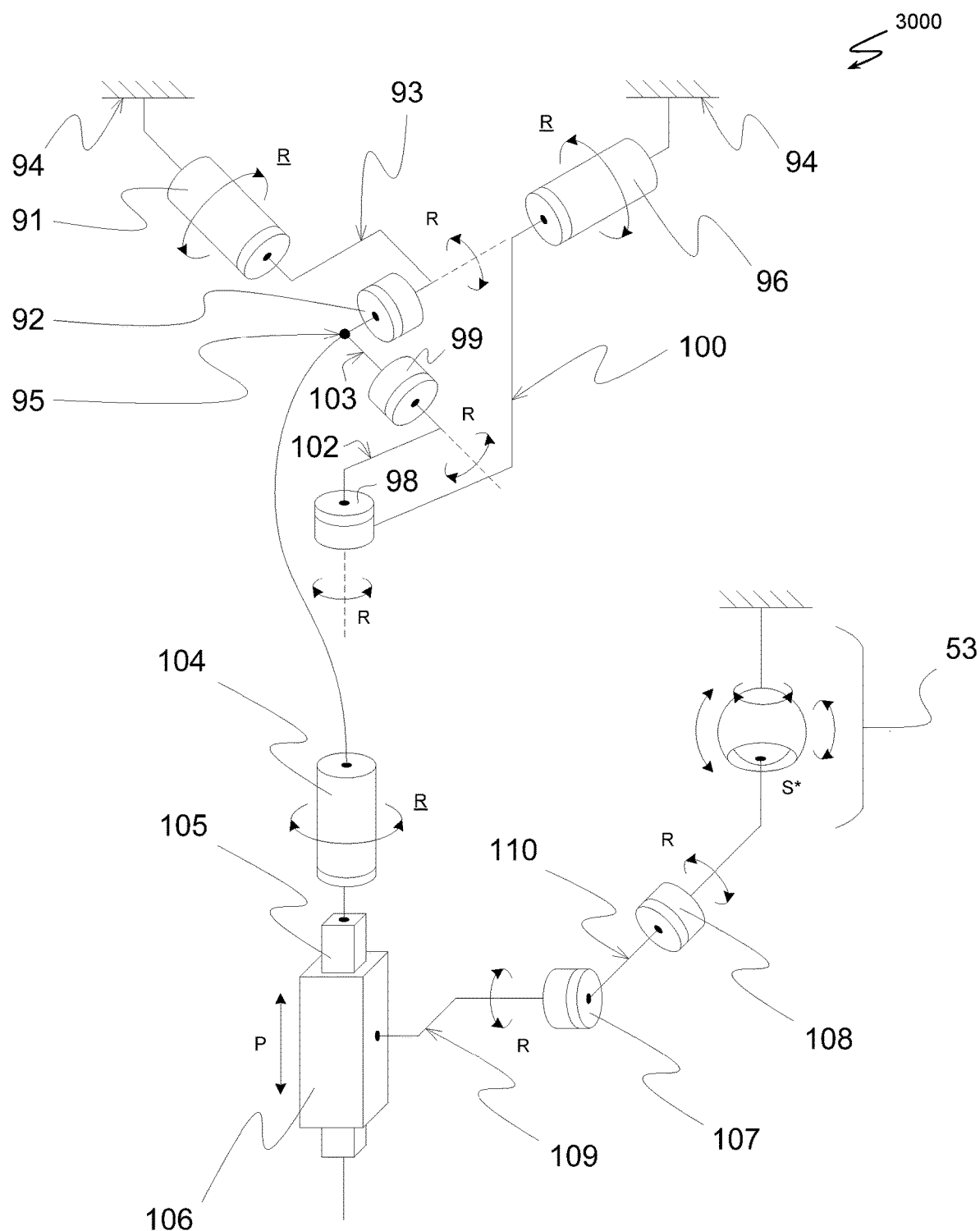
FIG. 12 is a mechanical schematic of an example of a device for guiding motions of a target showing joint and linkage components with joint motion capabilities where as labeled 'R' designates rotary joints, 'P' designates prismatic joints, 'S' designates ball-in-socket joints, underline designates active joints, no underline designates passive joints, and '*' designates the target joint for guidance.

In another embodiment of a device 3000 for guiding motions of 3-DOF joint systems depicted in FIG. 12, a rotary actuator and possible gearhead 91 are attached to a passive rotary joint 92 via a linkage 93 at one end and a base structure 94 at the other end. A rotary joint 92 sequentially connects to a moving plate 95. Additionally, a second rotary actuator and possible a gearhead 96 are attached to the base structure 94 at one end and two passive 1-DOF rotary joints 98-99 connected in series via linkages 100 and 102; the axes of rotation for the rotary joints 92, 98, and 99 are mutually perpendicular and intersect at a single point. Another linkage 103 connects a rotary joint 99 to the moving plate 95. The moving plate 95 is sequentially attached to a rotary actuator 104. For this specific embodiment, components 91-104 comprise the motion generator 16.

Next, a track component 105 attaches to the rotary actuator 104, and a sliding component 106 interfaces with the track component 105 to create a linear motion joint, such as for example a prismatic joint. In turn, the sliding component 106 connects to a passive 1-DOF rotary joint 107 which connects to another non-parallel and passive 1-DOF rotary joint 108 via consecutive linkages 109, 110. Sequentially, the 1-DOF rotary joint 108 attaches to one end of the true or quasi 3-DOF rotational joint of the passive target system 53. With respect to this embodiment, components 105-110 and any other required application-specific components comprise the motion transfer and target interfacing unit 27. Similar to the previous embodiments, this embodiment also involves connections from actuators 91, 96, 104 to the controller 28 and connections from relevant sensors to the motion detection and feedback unit 35.

In another implementation, the passive joints of the motion generator 16 and the motion transfer and target interfacing unit 27 can be replaced by active joints. For example, the passive prismatic joint composed of the track component 105 and the sliding component 106 can be replaced with an active linear actuator. For example, the motion guiding and detecting device can have the same components as the device 3000 of FIG. 12 except that the rotary actuator 104 can be replaced with a passive rotary joint and the passive prismatic joint can be replaced with the active linear actuator. In such implementation, the motion generator 16 can have two rotary actuators 91 and 96 and the motion transfer and target interfacing unit 27 can comprise one linear actuator, so that the device for guiding and detecting motions can still have at least three actuators for providing 3-DOF rotational motion of the target.

In all of the illustrated examples of the devices for guiding and detecting motions of the target joints (1000, 2000, 3000) or the motion assistance systems, the actuators and/or their drivers are mechanically connected into such devices/systems, however one can understand that such actuators and/or drivers can be remote from such devices/systems (e.g. can be placed in a backpack carried by a user) and the motion of the actuators can be transferred to where it is needed by a drive-by-wire mechanism, flexible shafts, gearing systems, etc., or wirelessly. The actuators can be selected from an electric motor, a pneumatic motor, a hydraulic motor or any other motor or combination thereof.

Figure 13:
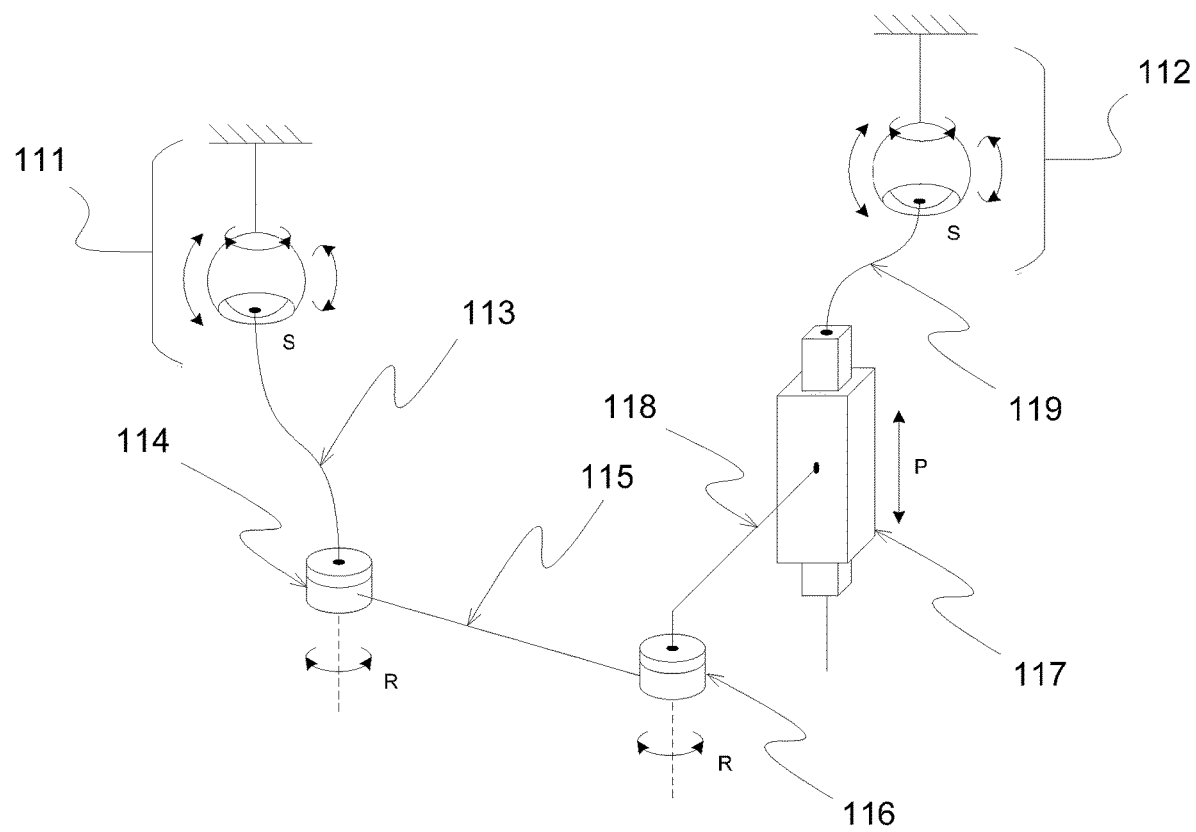
FIG. 13 is a mechanical schematic of an example of a motion transfer and target interfacing unit that connects a 3-DOF motion-generation unit and a target joint where two adjacent rotary joints have parallel axes and form a four-bar mechanism with adjacent linkages. As labeled, 'R' designates rotary joints, 'P' designates prismatic joints, and 'S' designates ball-in-socket joints or a system of joints that act together to permit spherical motions.

FIG. 13 depicts the mechanical structure of one embodiment for the motion transfer and target interfacing unit 27. As already mentioned herein above, the motion transfer and target interfacing unit 27 is used to transfer the 3-DOF motions generated by the motion generator 16 to the target joint 53. In the illustrated embodiment of FIG. 13, the 3-DOF motions are transferred from one spherical joint or joint system 111 to another spherical joint or joint system 112. In such case, the joint or joint system 111 represents the 3-DOF motion generator 16 while joint or joint system 112 represents the target 53. Person skilled in the art would understand that the motion transfer and target interfacing unit 27 can transfer the motions from the joint or joint system 112 (which in this case can be the motion generator 16) to the joint or joint system 111 (which can be the target 53) without departing from the scope of the invention. The motion transfer unit 27 can comprise a linkage 113 connecting the motion generator (joint or joint system 111) to a rotary joint 114. Another linkage 115 connects the rotary joint 114 to another rotary joint 116 which is connected to a prismatic joint 117 via a linkage 118. Another linkage 119 connects the prismatic joint 117 to the target (spherical joint or joint system 112). In FIG. 13, the linkages are not meant to depict any special geometric relation between joint axes (i.e. perpendicularity, parallelism, etc.) except that the rotary joint 114 and the rotary joint 116 have parallel axes and thus form a four-bar mechanism with all adjacent linkages. In cases where the joint or joint system 111 is the target 53, the linkage 113 may be comprised of several linkage structures affixed to each other. If joint or joint system 112 is the target 53, the linkage 119 may be comprised of several linkage structures affixed to each other.

Figure 14:
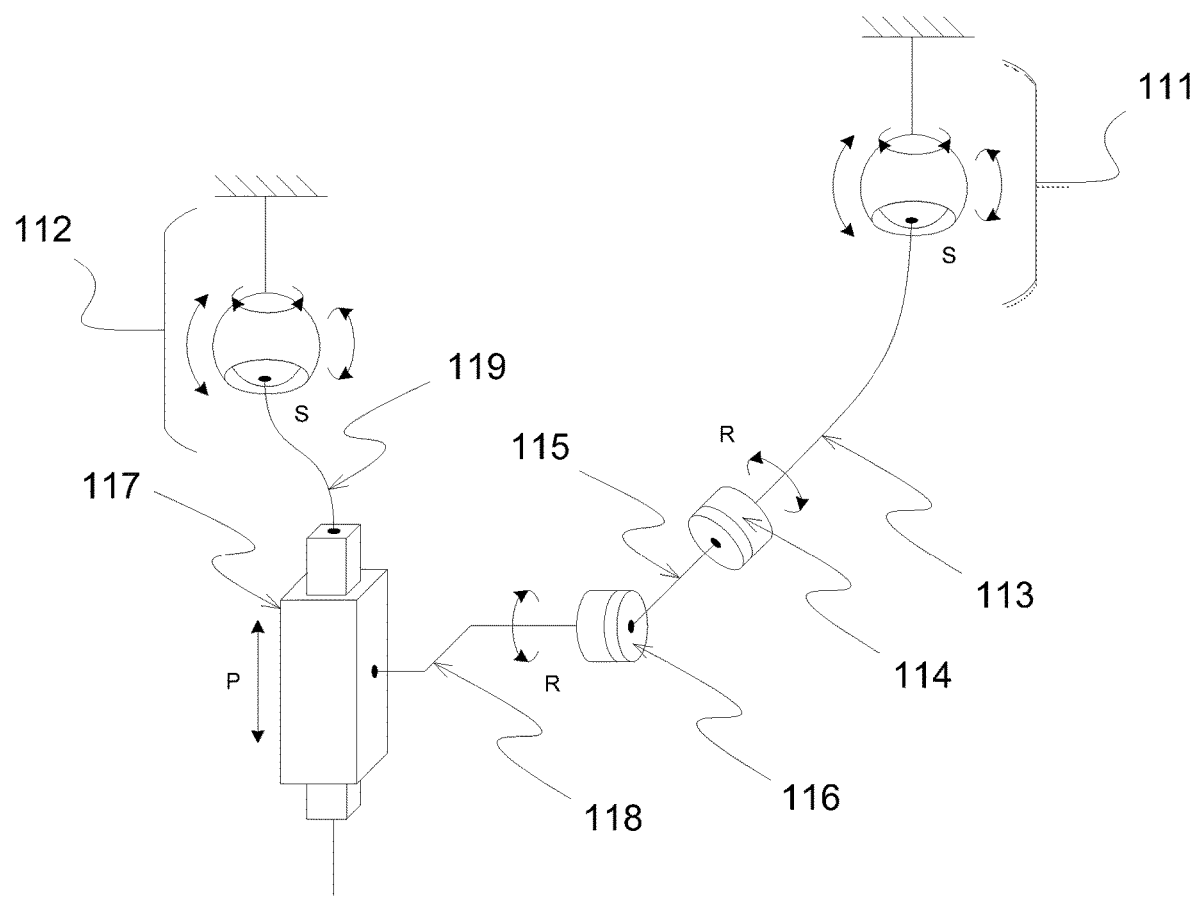
FIG. 14 is a mechanical schematic of an example of a motion transfer and target interfacing unit where two adjacent rotary joints are combined to form a 2-DOF universal joint and the axes of the two adjacent rotary joints are perpendicular. As labeled, 'R' designates rotary joints, 'P' designates prismatic joints, and 'S' designates ball-in-socket joints or a system of joints that act together to permit spherical motions.
Figure 15:
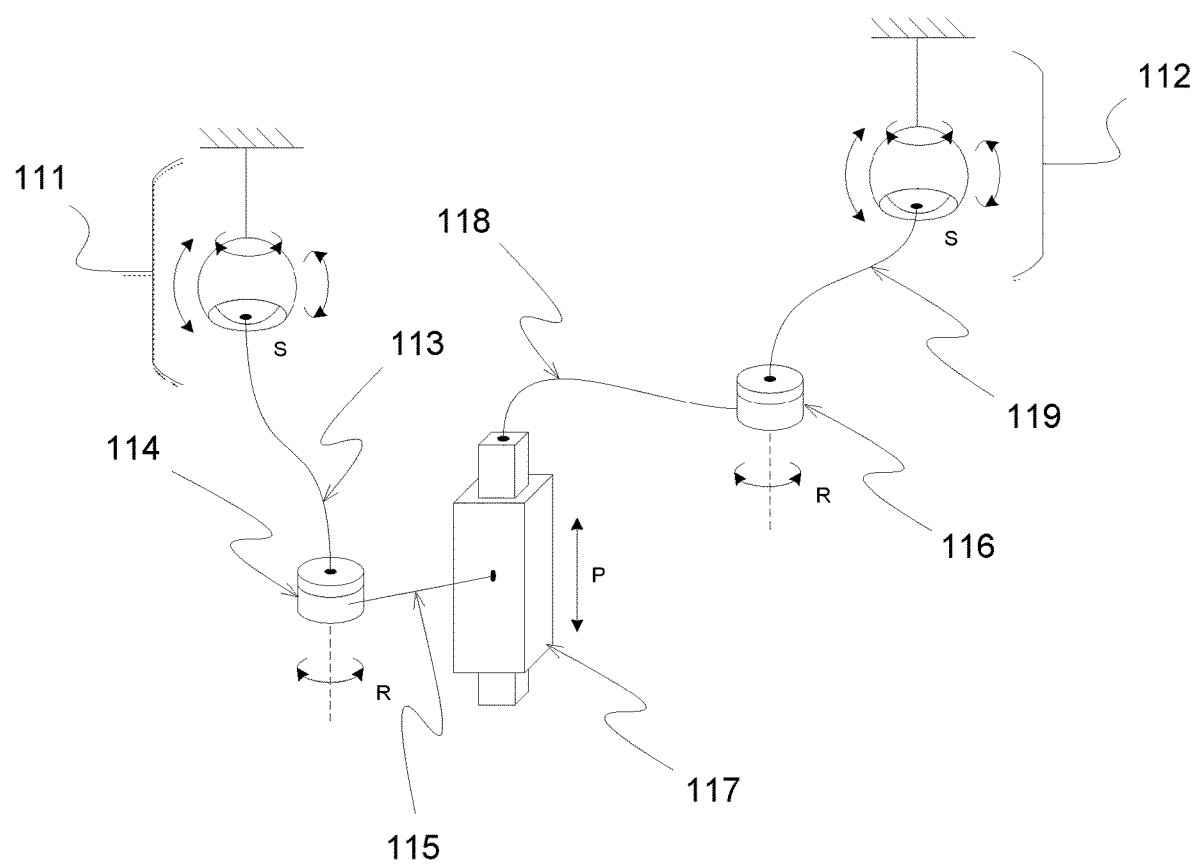
FIG. 15 is a mechanical schematic of the motion transfer and target interfacing unit of FIG. 13 where placements of a rotary joint and a prismatic joint are being swapped compared to the motion transfer and target interfacing unit illustrated in FIG. 13.
Figure 16:
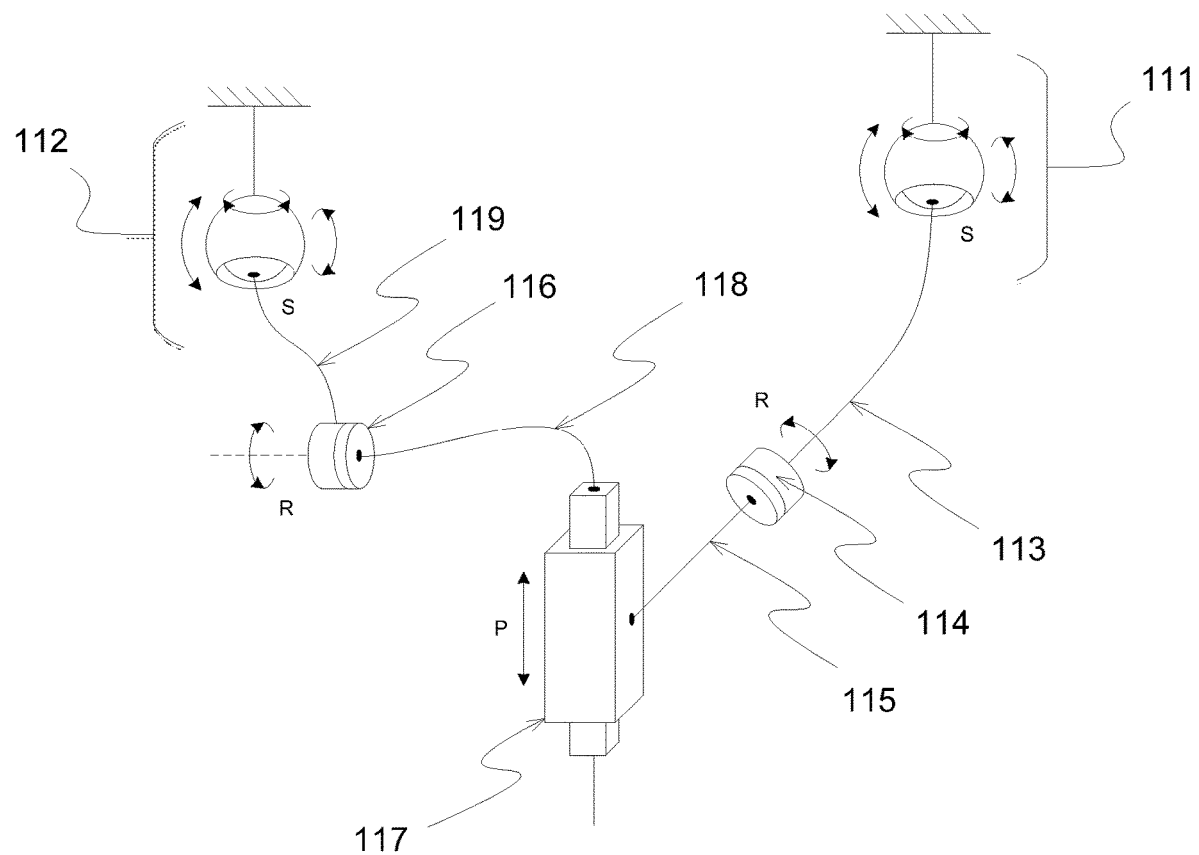
FIG. 16 is a mechanical schematic of the motion transfer and target interfacing unit of FIG. 14 where placements of a rotary joint and a prismatic joint are being swapped compared to the motion transfer and target interfacing unit illustrated in FIG. 14.

FIG. 14 depicts the motion transfer and target interfacing unit 27 of FIG. 13 where the adjacent rotary joints 114 and 116 do not have parallel axes. For example, rotary joints 114 and 116 can have perpendicular axes and the two adjacent rotary joints may or may not be combined to form a 2-DOF universal joint. In the illustrated example, the link 115 can have zero (or close to zero) length and the rotary joints 114 and 116 can have perpendicular axes. Combining the joints by this method can achieve a more compact mechanical structure for the motion transfer and target interfacing unit 27. The motion transfer and target interfacing unit 27 illustrated in FIG. 15 have swapped a position of the rotary joint 116 and the prismatic joint 117 in order to also create a more compact mechanical structure for some applications. Same as with respect to the motion transfer and target interfacing unit 27 illustrated in FIG. 13, the linkages illustrated in FIG. 15 are not meant to depict any special geometric relation between joint axes (i.e. perpendicularity, parallelism, etc.). FIG. 16 depicts the motion transfer and target interfacing unit 27 of FIG. 14 with the placements of the rotary joint 116 and the prismatic joint 117 being swapped.

Figure 17:
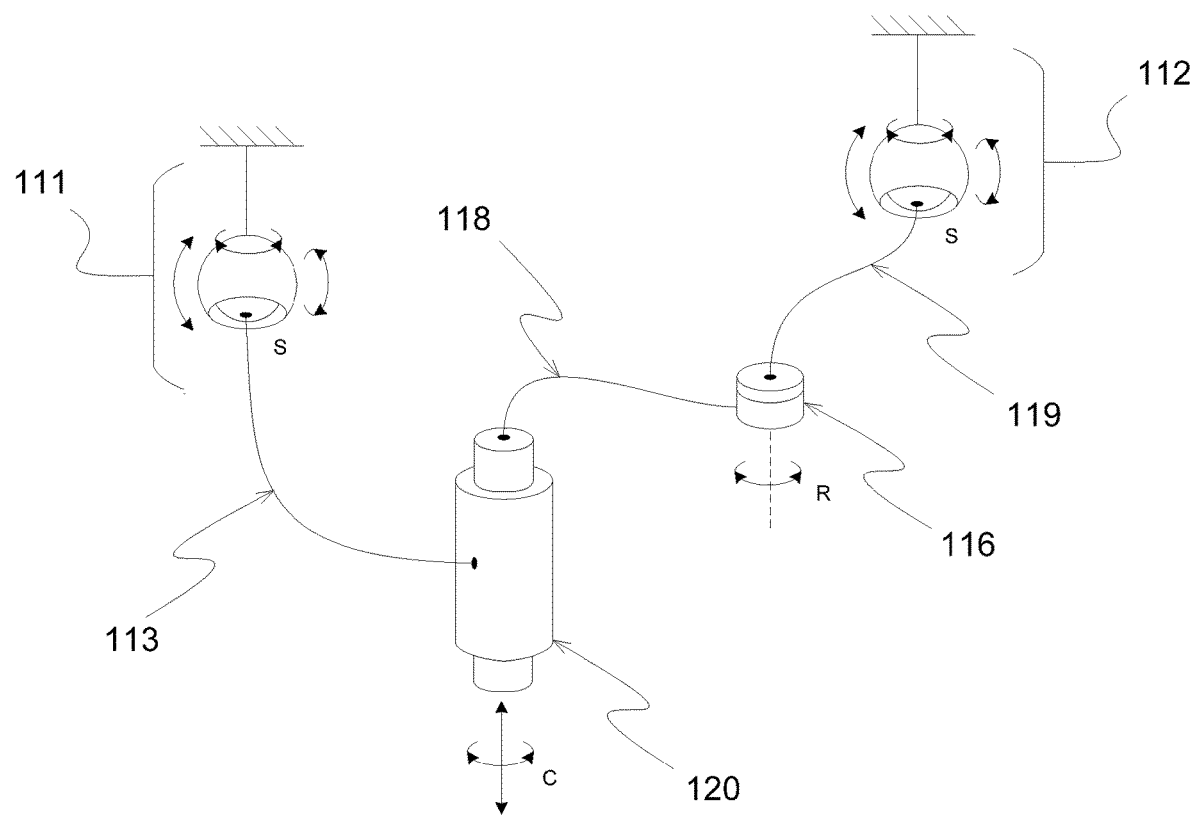
FIG. 17 is a mechanical schematic of the motion transfer and target interfacing unit of FIG. 15 in which a rotary joint and a prismatic joint are combined as a cylindrical joint.
Figure 18:
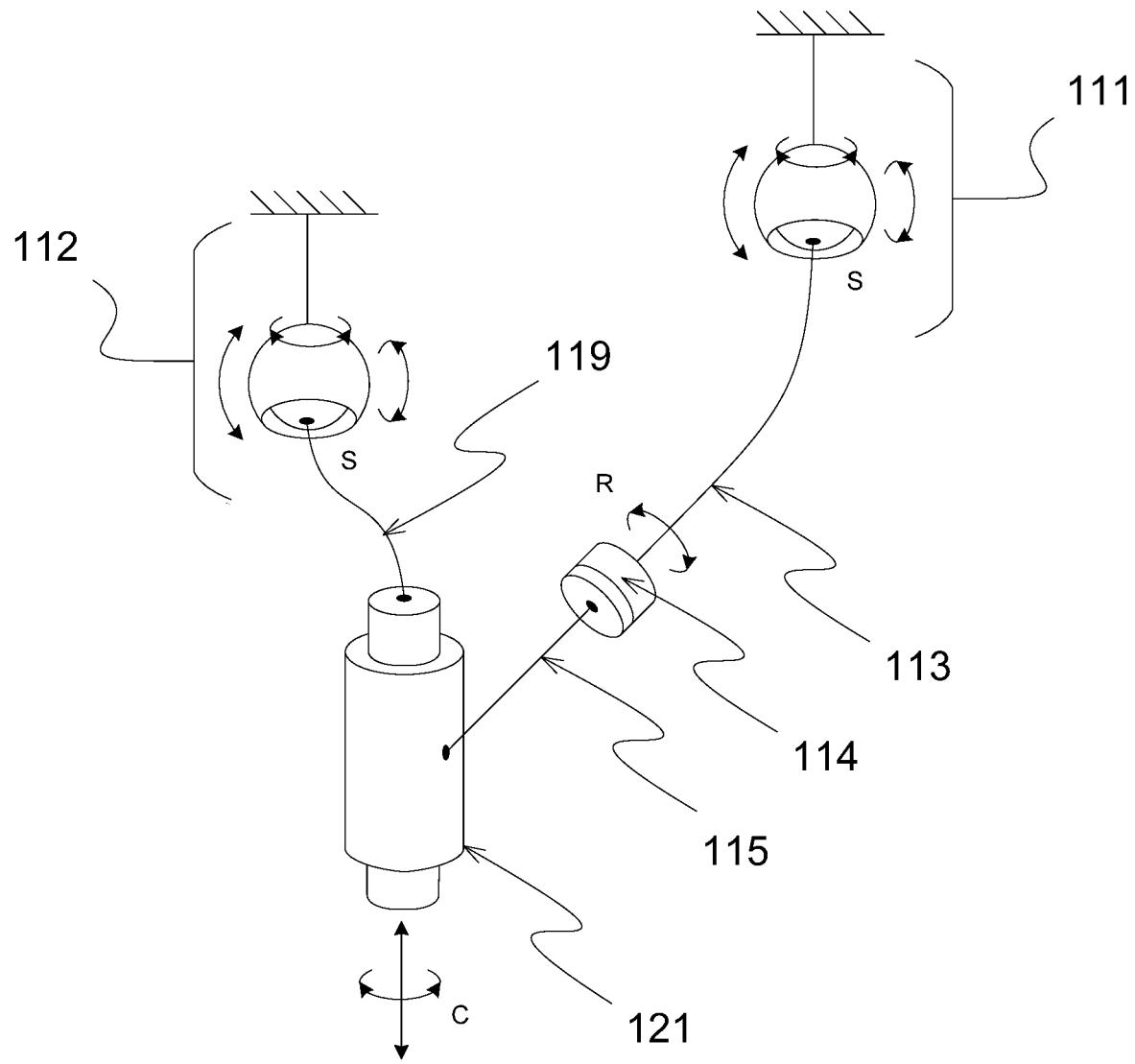
FIG. 18 is a mechanical schematic of the motion transfer and target interfacing unit of FIG. 16 in which a rotary joint and a prismatic joint are combined as a cylindrical joint.

FIGS. 17 and 18 each depicts the motion transfer and target interfacing unit 27 of FIGS. 15 and 16 where the length of the respective linkage 115, 118 is zero. With respect to the motion transfer and target interfacing unit 27 of FIG. 18, the axes of the rotary joint 114 and the prismatic joint 117 are parallel, and the rotary joint 114 and the prismatic joint 117 are combined as a cylindrical joint 120 to increase compactness and simplicity of the mechanical structure. Similarly, with respect to the motion transfer and target interfacing unit 27 of FIG. 18, the axes of the rotary joint 116 and the prismatic joint 117 are parallel, and the rotary joint 116 and the prismatic joint 117 are combined as a cylindrical joint 121 to increase compactness and simplicity of the mechanical structure.

Figure 19:
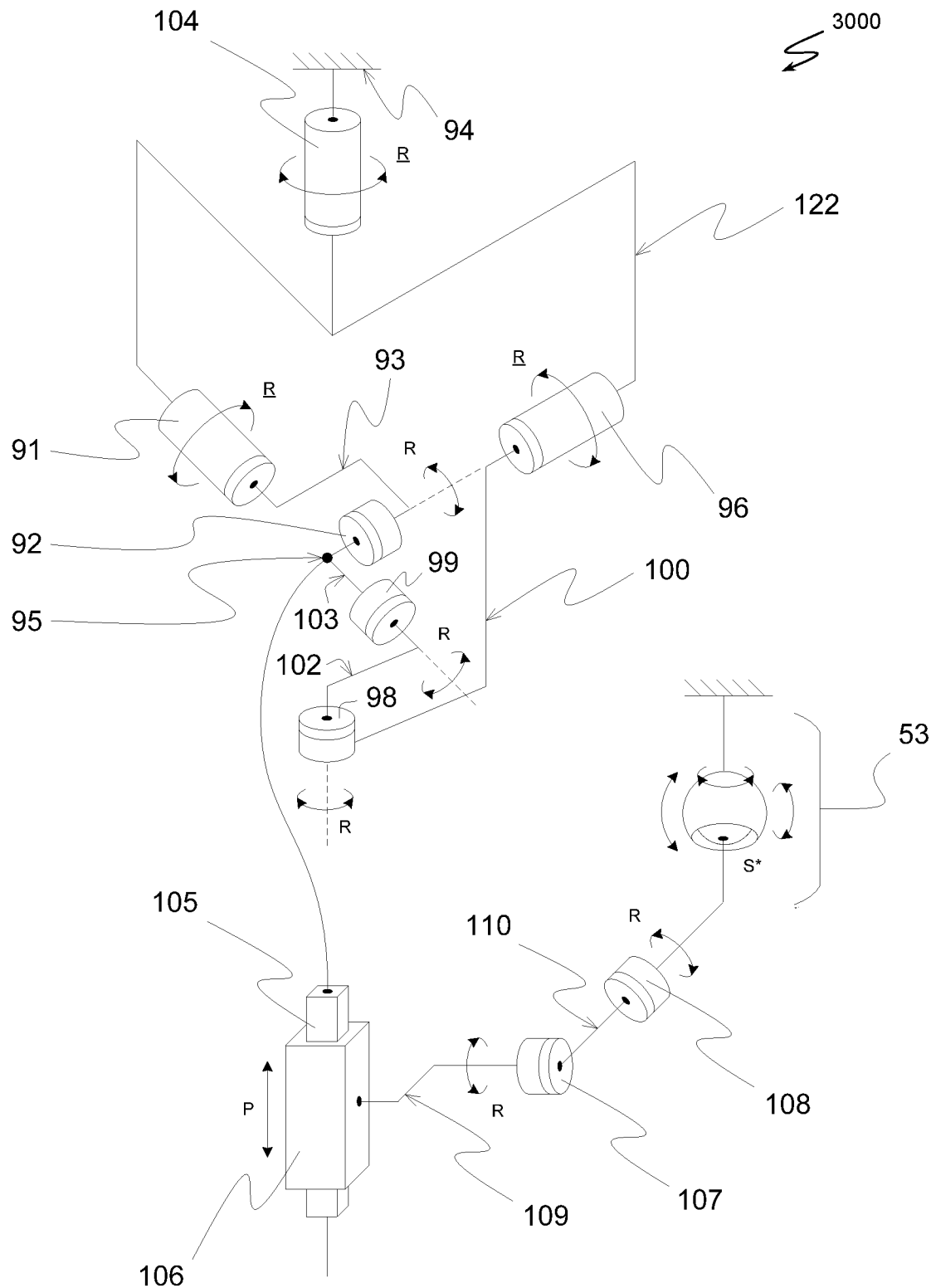
FIG. 19 is a mechanical schematic of an example of a device for guiding motions of a passive 3-DOF joint system in which a placement of one rotary actuator is moved between a base structure and the other two rotary actuators.

FIG. 19 depicts an example of the device 3000 for guiding motions of a passive 3-DOF joint system of FIG. 12 except that the placement of the rotary actuator 104 is moved between the base structure 94 and the rotary actuators 91 and 96. Attendant to this adjustment is the introduction of a linkage 122, which connects an output shaft of the rotary actuator 104 to both rotary actuators 91 and 96.

Figure 20:
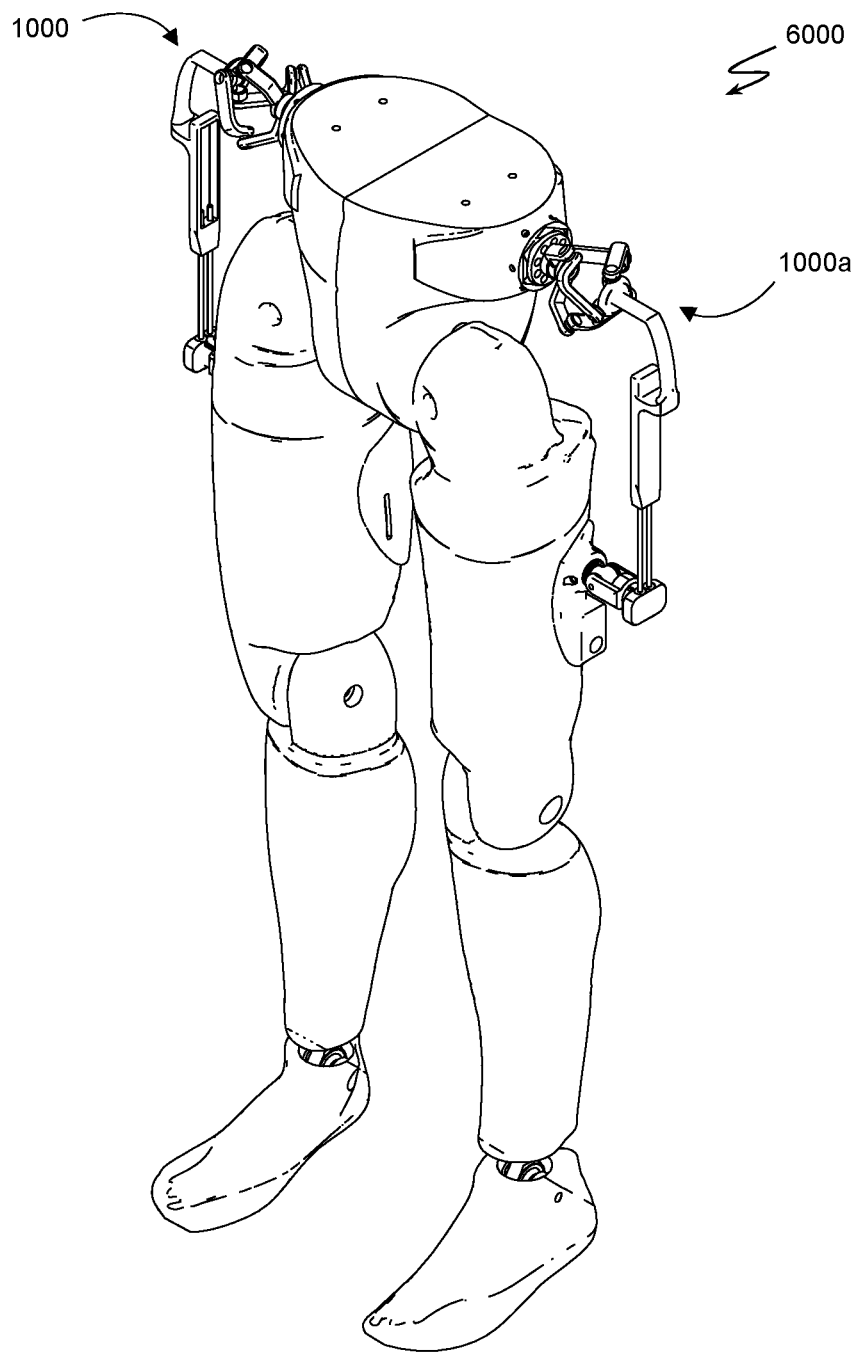
FIG. 20 is a perspective view of an example of motion assistance system showing two devices for guiding motions of hip exoskeleton target joints in which rotary actuators of a motion generator are aligned coaxially.

In one implementation, any of the devices 1000, 2000 or 3000 disclosed herein can be used as components of a motion assistance system, such as an exoskeleton, that can be used to move the joints and the body segments of a user. The motion assistance system can comprise at least two of the devices 1000, 2000, 3000 in communication with each other to generate a coordinated movement of two or more different joints and body segments (targets). For example, a single controller can be used to control the movement of the two or more motion guiding and detecting devices 1000, 2000, 3000 interconnected to form the motion assistance system. The controller can identify user's intention based on the information obtained from the sensors of the motion detection and feedback units and can then send the appropriate control signal to the drivers of the actuators of the motion generation units and the motion transfer and target interfacing units (in cases where the motion transfer unit comprises an actuator) to generate a specific motion. The input to the controller might be from the user's nerve system (via electroencephalograph), a voice recognition unit, feet contact force, a tracking system that can, for example, detect a predetermined head motion or eye tracking, etc. The controller can also use sensors (e.g. IMU sensors) input data to detect the balance of the user and to maintain it by providing proper triggering commands to the actuators. In one embodiment, the motion assistance device (i.e. the exoskeleton) can be equipped with an airbag or an active cushion system that can be deployed upon a fall detection. The airbag can use conventional chemical reaction for inflation or can use other reversible methods such as compressed air, high speed fans, or compressible soft materials such as polyurethane foam. An actuation mechanism, such as the drivers of the actuators, can be electric, pneumatic, hydraulic, etc. In case of electric drivers, the motion assistance system (exoskeleton) can be battery powered and can be equipped with a battery and a power management circuit board. The motion assistance system can be configured to move the user to a safe body position, such as sitting or laying, in case of emergency. For example, FIG. 20 depicts a motion assistance system 6000 showing two devices 1000, 1000a for guiding motions of hip exoskeleton joints (two hip exoskeleton modules 1000, 1000a) in which rotary actuators of the motion generator 16 are aligned coaxially.

Figure 21:
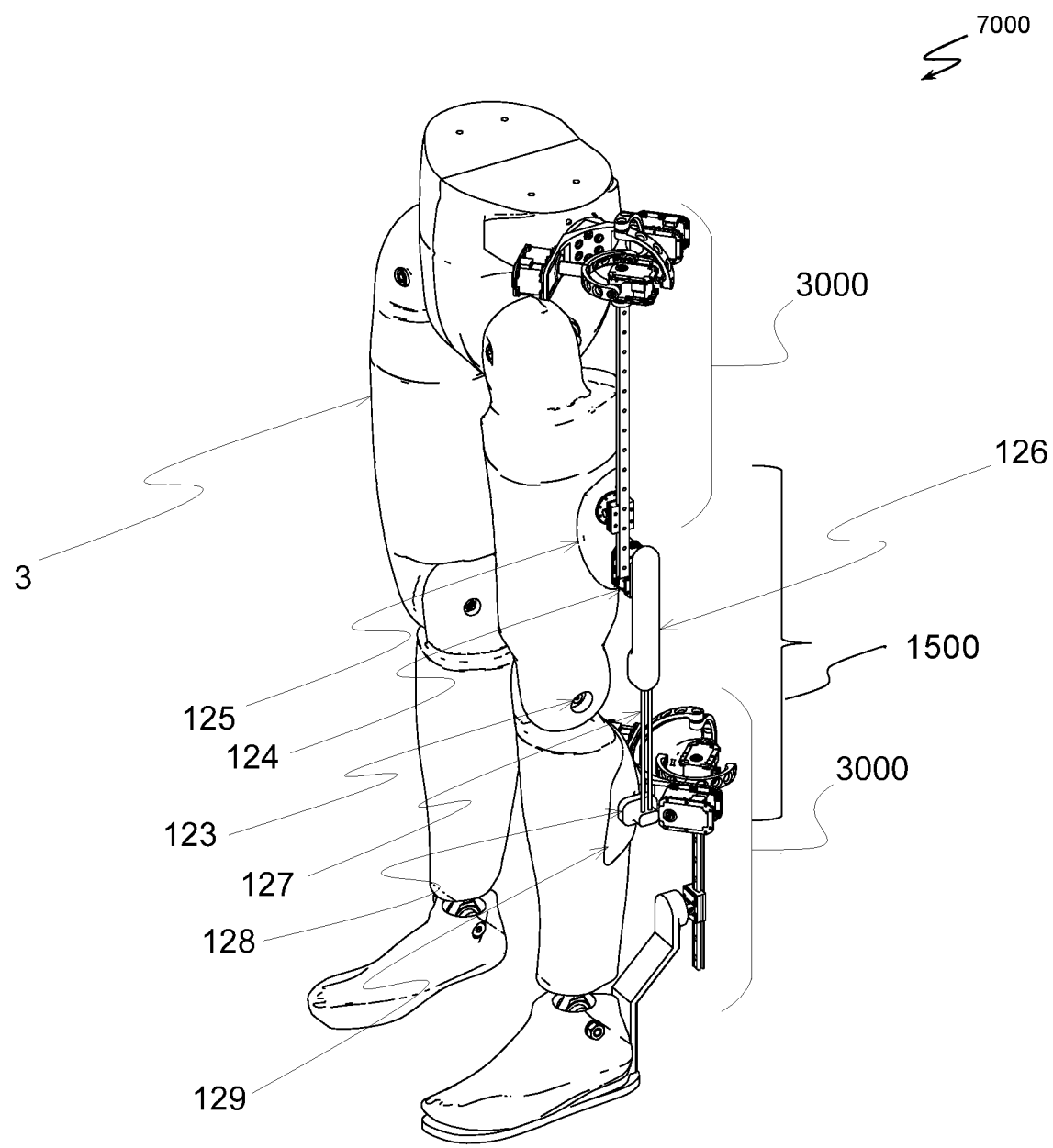
FIG. 21 is a side view of an example of a motion assistance system showing three exoskeleton modules (motion guiding devices) that are connected in series along a user's leg to produce a complete lower-limb exoskeleton system.

FIG. 21 shows another motion assistance system showing three exoskeleton modules (motion guiding and detecting devices) that are connected in series along a user's leg to produce a complete lower-limb exoskeleton system 7000. For example, one of the exoskeleton modules can be the motion guiding and detecting device 3000 (illustrated in FIG. 12) that can be attached at the pelvis and upper leg of the user 3, surrounding the biological hip joint. Attached across the user's knee joint 123, a knee exoskeleton module 1500 is comprised in general of a 3-DOF motion guiding and detecting device as explained herein before or it can comprise a rotary actuator 124 (or a linear actuator), which is fixed to an upper leg orthotic 125 and is connected to a track linkage 126 at its output shaft. A sliding linkage 127 interfaces with the track linkage 126 as a linear-motion joint. The lower end of the sliding linkage 127 attaches to a passive rotary joint 128, which in turn connects to the lower leg orthotic 129. The third exoskeleton module can also be a motion guiding device 3000 that surrounds the user's ankle joint to guide its motions.

Figure 22:
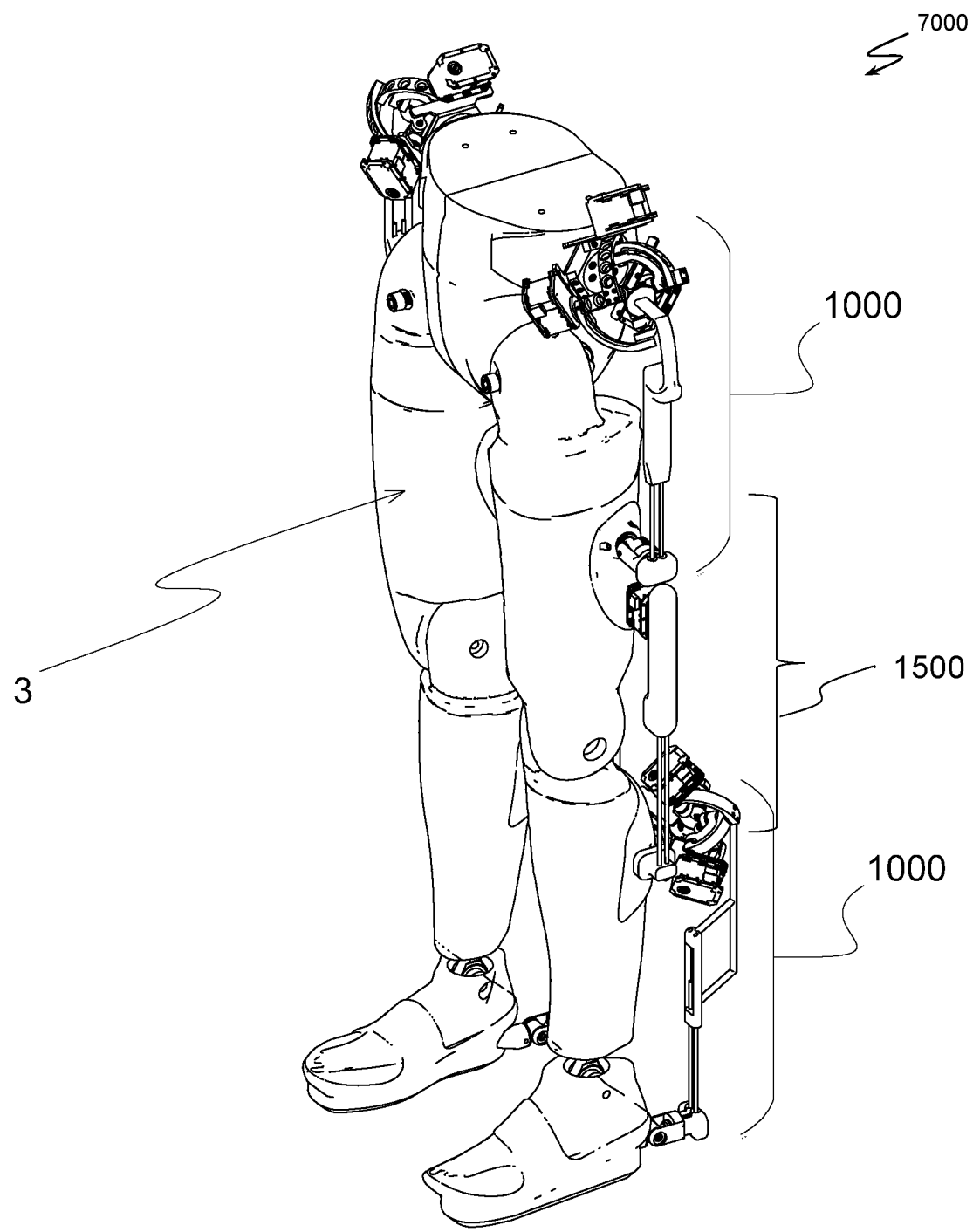
FIG. 22 is a side view of another example of a motion assistance system showing three exoskeleton modules that are connected in series along a user's leg to produce a complete lower-limb exoskeleton.

Similar to FIG. 21, FIG. 22 depicts the motion assistance system 7000 with three exoskeleton modules that are connected in series along a user's leg to produce a complete lower-limb exoskeleton. The two of the exoskeleton modules can be designed as the motion guiding and detecting device 1000 which can be attached to the user 3 surrounding the biological hip joint and the biological ankle joint. The knee exoskeleton module can be equivalent to the device 1500 described with respect to FIG. 21.

Figure 23:
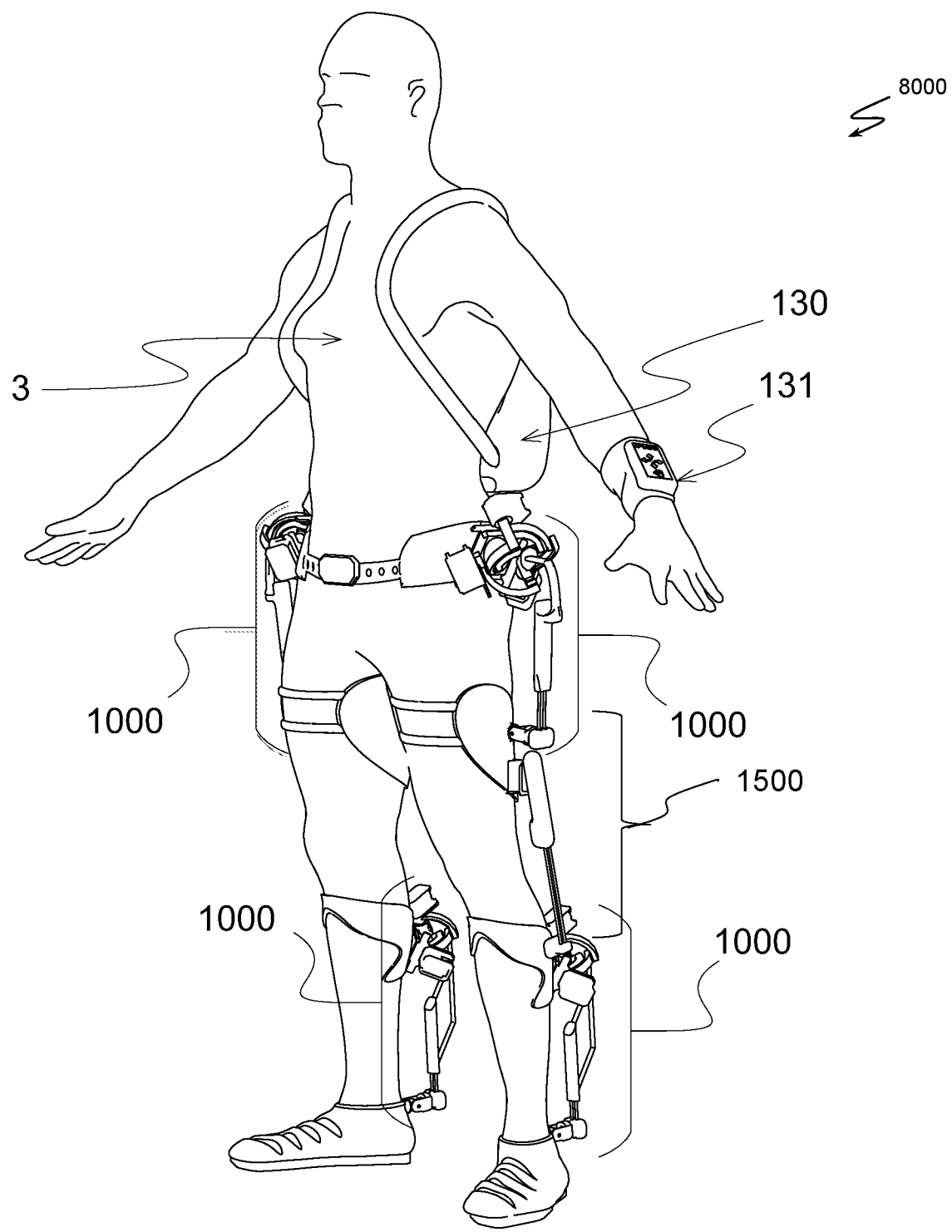
FIG. 23 is a perspective view of an embodiment of a motion assistance system mounted to a user and used as a personal-use mobility aid with several exoskeleton modules that work in synchronicity with each other and peripheral components.

FIG. 23 depicts an example of a motion assistance system 8000 in which several exoskeleton modules work in synchronicity with each other and peripheral components to comprise a personal-use mobility aid. For example, the motion guiding and detecting device 1000 can be mounted to the user's body 3 and used for guiding motions of the hip and ankle target joints. The knee exoskeleton modules 1500 can also be mounted to the user surrounding the knee joint and can be used to guide motions of the biological knee target joints. The system 8000 can further comprise a backpack that contains a portable power supply and attendant electronics 130 required to power the mobility aid system 8000. In one implementation, the drivers of the actuators of the motion guiding and detecting devices can also be placed in the backpack. A wearable electronic device 131 can communicate wirelessly with the controller(s) 28 of the motion guiding devices 1000, 1500 to permit touch-screen input and/or voice input and human-machine interfacing.

Figure 24:
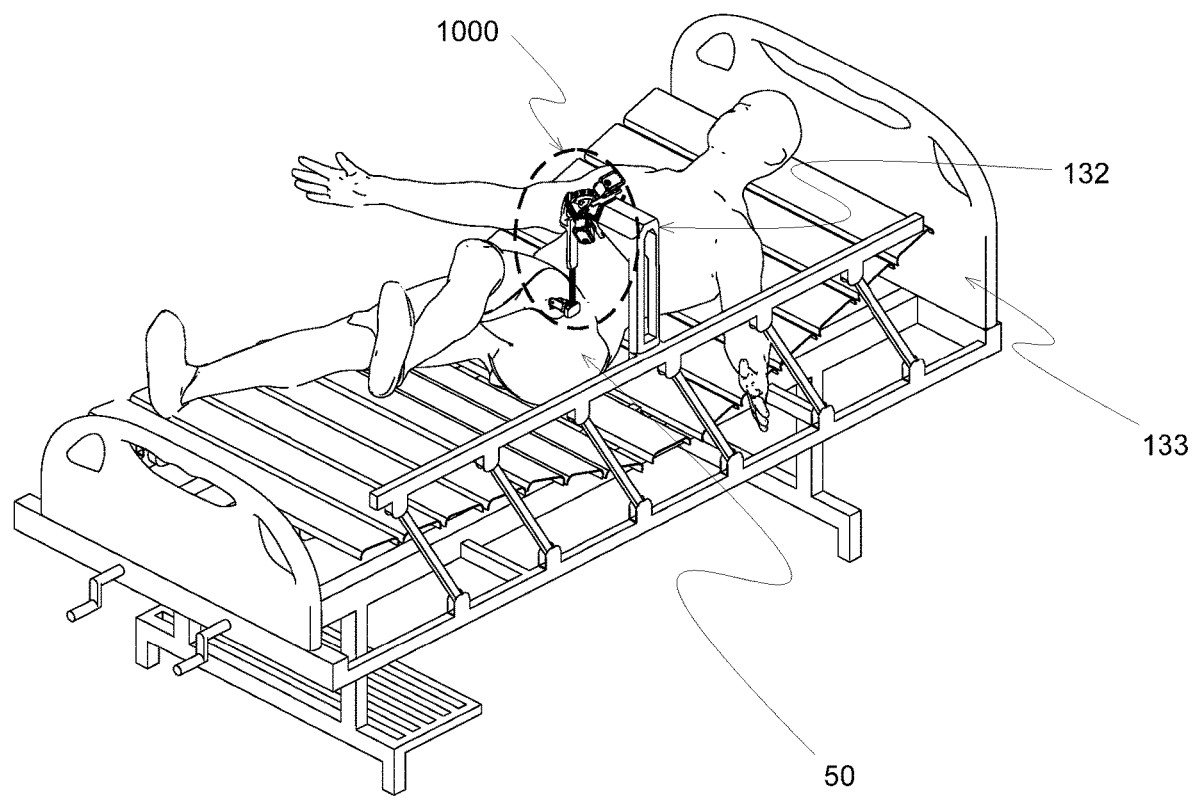
FIG. 24 is a perspective view of an example of a motion guiding device used for positioning another structure, such as an upper leg, and hold the upper leg in a locked position.

In one embodiment, the components of the exoskeleton can be rearranged to convert it to a motion guiding system for positioning another structure. One example of such application can be an orthopedic surgical system to assist a surgeon to position limbs in a desired orientation. The motion guiding and detecting device can be single device 1000, 2000, 3000 or a combination of two or more of such devices 1000, 2000, 3000 that are in communication or interconnected together. The motion guiding and detecting device can be fixed to an external fixture so that the moving platform (e.g. moving plate 14) of the actuators can be connected to the structure to be positioned via the motion transfer mechanism 27. The desired position of the structure can then be achieved by commanding the actuator system via its controller. FIG. 24 depicts a motion guiding device 1000 in which the base of the device 1000 is connected to a mounting arm 132, which in turn attaches to the operating table 133. The mounting arm 132 is capable of spatially positioning the device's base as well as clamping the base to a fixed position with respect to the operating table 133. The device 1000 can then be used to lift and position the leg of the patient (or other human body segments) and hold such leg in a locked position so that the patient's hip 50 is positioned and orient in an appropriate position for surgery. The input interface for the user can be set with a joystick, a virtual reality unit, a keyboard, voice recognition unit or a pre-set orientation parameters can be set in an options module. In one implementation, the actuators of the motion guiding and detecting device can also be replaced with lockable joints. In this arrangement, the surgeon/operator can move the leg/object until the desired position/orientation is reached and then lock the position/orientation by locking the actuators/joints of the motion guiding and detecting device.

Figure 25:
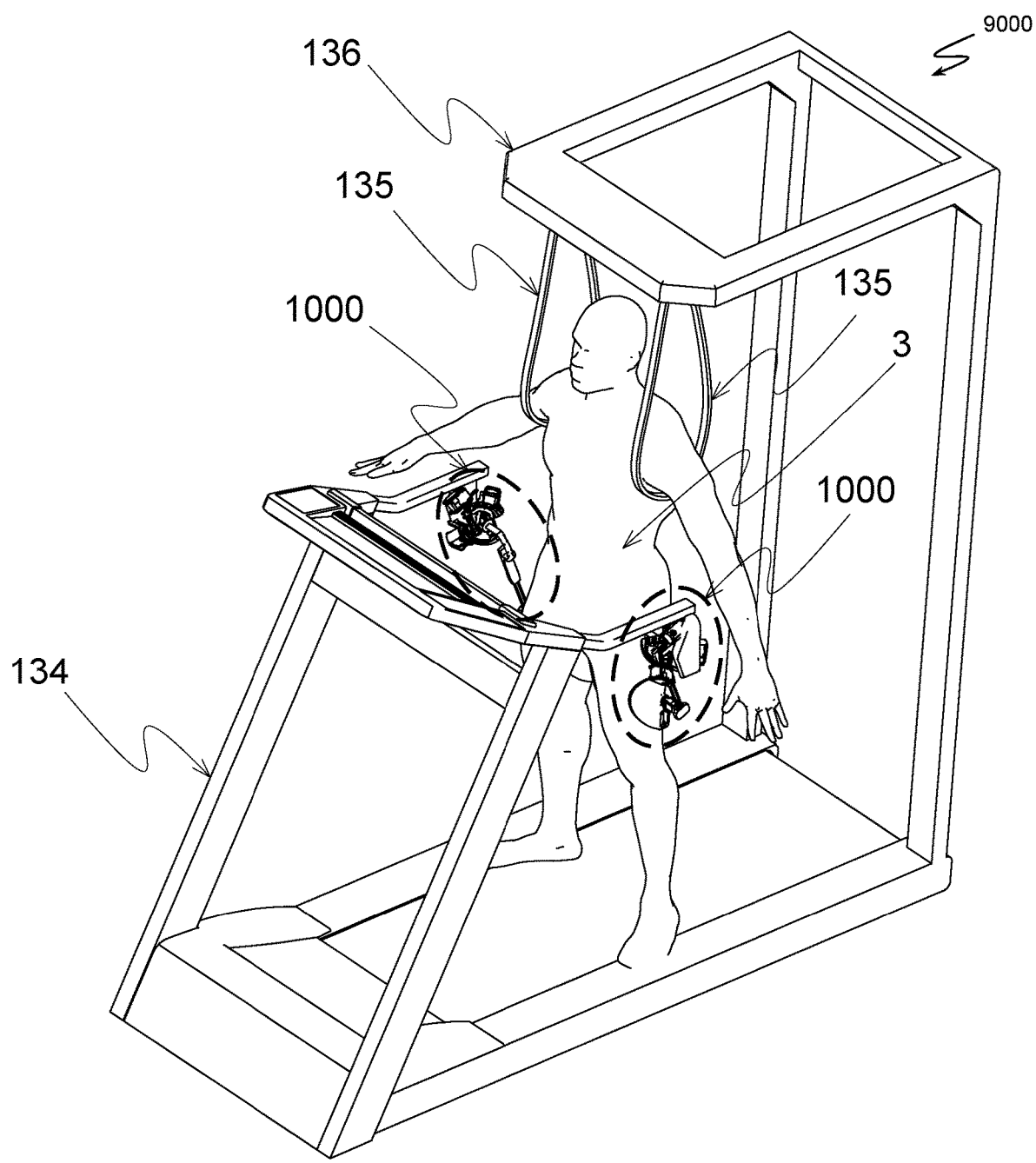
FIG. 25 is a perspective view of an example of a motion assistance system mounted to a user and used as a rehabilitation tool.

In another implementation, the motion assisting system of the present invention can be employed as a robotic rehabilitation tool. For example, a physiotherapist can secure a patient to the motion assistance exoskeleton system using the straps in order to support the weight of the user and can then program the exoskeleton to help patients limb through some repetitive exercises. FIG. 25 depicts one example of a motion assistance system 9000 used as a rehabilitation system. The system 9000 comprises two motion guiding and detecting devices 1000 where their bases are attached to a treadmill device 134. The other ends of the devices 1000 are attached to the upper legs of a human user 3. The user's body weight is supported by straps 135 suspended from a crane 136 attached to the treadmill device base. The devices 1000 guide the user's hip joint motions during gait training exercises on the treadmill device 134. In one implementation, only one motion guiding device 1000, 2000, 3000 can be used instead of the lower limb exoskeleton, for example for ankle rehabilitation purposes. The therapists can monitor the progress of patients on site or remotely by receiving the processed data from the exoskeleton's controller. The data can be accessed by direct log into the controller or the data can be transferred to the therapists via wired/wireless data transfer. The therapist can also remotely modify the exercise set-up based on patients' progress.

Figure 26:
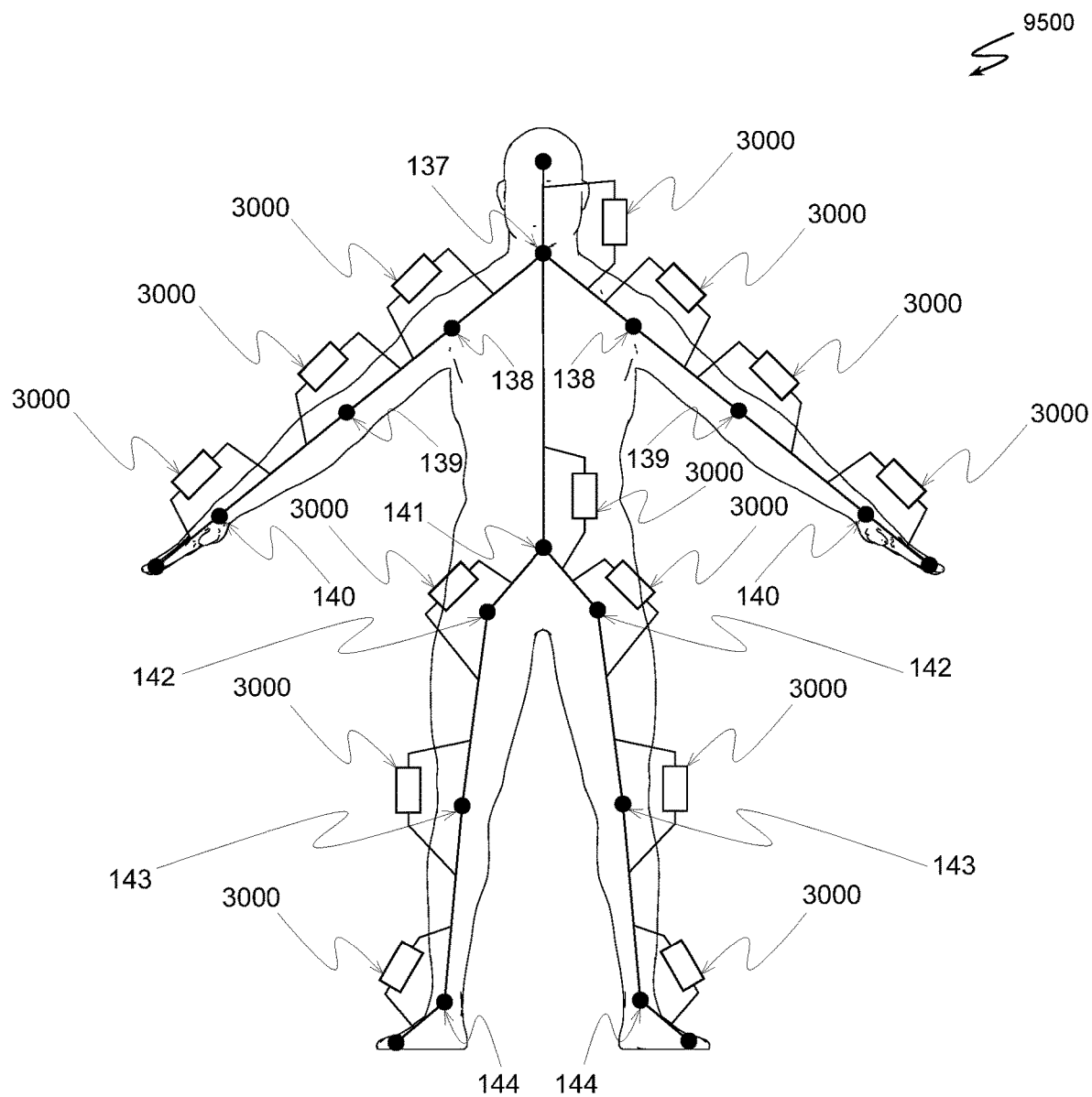
FIG. 26 a mechanical schematic of an example of a motion assistance system mounted to a user and used as a full-body motion capture device.

In one implementation, the motion assisting system (e.g. an exoskeleton) can be used as a motion capturing device. The system can comprise a first motion guiding and detecting device for detecting and/or guiding motion of a first target joint and at least one additional motion guiding device for detecting and/or guiding motion of another target joint. The motion capture system is secured to a user using mounting means such as for example straps and orthotics. In this aspect, the actuators of the motion generator and the motion transfer and target interfacing unit (if any) may or may not be present. For example, the actuators can be replaced by sensors, e.g. encoders, linear/rotary potentiometers, etc., and an inverse kinematic algorithm programmed in the controller can use the data to calculate the accurate orientation of the human target joints and the body segments' position. For example, FIG. 26 depicts an embodiment of a motion assistance system 9500 used as a full-body motion capture device. The system 9500 can comprise a plurality of motion guiding devices (e.g. devices 3000) that can be attached by an non-intrusive means to the human body surrounding the neck 137, shoulders 138, elbows 139, wrist 140, lower back 141, hips 142, knees 143, and ankles 144. The motion guiding and detecting devices in such system 9500 may not include actuators but rather the active joints can be substituted with passive equivalents. So, the user can produce a motion to any or all of the joint targets and the plurality of sensors can detect such motion (produced by the user) by measuring the motion (position and orientation) of the passive joints of the motion capturing system 9500 and the controller can calculate the target joints motion using an algorithm programmed in the controller. In some embodiments of the system 9500 the controller 28 may also be omitted and the motion data can be temporarily stored in the motion detection and feedback unit 35 of each device 3000, and later transferred to a computer (an external controller) for further processing. Alternatively, in another embodiment, the active joints of the motion guiding and detecting devices 3000 and the controller(s) 28 may not be omitted and the system 9500 can communicate with an external Virtual Reality (VR) or an Augmented Reality (AR) system. An additional controller can be in communication with the first motion guiding and detecting device and the at least one additional motion guiding and detecting device to coordinate guidance of the multiple targets. The motion detection and feedback unit(s) can be in communication with the external virtual or augmented reality systems. In this case, the actuators do not create any resistance until the user physically contacts something in the virtual or augmented reality environment, at which time the actuators engage to emulate a tactile response (e.g. force feedback) to a virtual entity. For example, this embodiment can by applied in the gaming industry where a gamer may need to have a better interaction with the environment. The controller can be pre-programmed to command the actuators to resist motions in certain directions/orientations or to apply forces in certain directions/orientations. The system 9500 can also be used in training applications, such as sports, where inaccurate/incorrect motions will be restricted while the accurate/correct motions will be facilitated (or not interfered) by the exoskeleton.

In one implementation, the device 1000, 2000, 3000 or the motion assistance system can be used for a motion augmentation. For example, the user can benefit from the extra power that the system (e.g. exoskeleton) can provide for commuting longer distances and carrying heavier loads. In such implementation, the whole exoskeleton or its subcomponents (individual motion guiding and detecting devices) can be individually employed for the motion augmentation depending on each specific application. In this arrangement, sensors such as IMU, force sensors (e.g. measuring foot pressure), EMG, ECG, encoders, etc. will be used to identify user intentions. Based on that, the controller will generate commands for the actuators to produce torques to assist human joints and muscles in producing the motion In another embodiment, the actuators can be replaced by lockable joints. In this arrangement, an operator can manually move the structure to be positioned until the desired position is achieved while the motion guiding device is attached. The actuators will not create any resistance against the motion until the desired position is reached. The operator can then lock the lockable joints to maintain the position.

In another embodiment, the full body exoskeleton or its subcomponents, e.g. hip subcomponent, can be used as a fall prevention device, where the controller can comprise a balance detection algorithm which can monitor the users gait via signals received from sensors, such as one or more encoders, IMU systems, foot force sensors etc. The controller will then command the exoskeleton or its subcomponents to force the lower body to move into a position which increase the stability of the user. The system can be active or passive during other normal mobility actions.

While particular elements, embodiments and applications of the present disclosure have been shown and described, it will be understood, that the scope of the disclosure is not limited thereto, since modifications can be made by those skilled in the art without departing from the scope of the present disclosure, particularly in light of the foregoing teachings. Thus, for example, in any method or process disclosed herein, the acts or operations making up the method/process may be performed in any suitable sequence and are not necessarily limited to any particular disclosed sequence. Elements and components can be configured or arranged differently, combined, and/or eliminated in various embodiments. The various features and processes described above may be used independently of one another, or may be combined in various ways. All possible combinations and sub-combinations are intended to fall within the scope of this disclosure. Reference throughout this disclosure to "some embodiments," "an embodiment," or the like, means that a particular feature, structure, step, process, or characteristic described in connection with the embodiment is included in at least one embodiment. Thus, appearances of the phrases "in some embodiments," "in an embodiment," or the like, throughout this disclosure are not necessarily all referring to the same embodiment and may refer to one or more of the same or different embodiments. Indeed, the novel methods and systems described herein may be embodied in a variety of other forms; furthermore, various omissions, additions, substitutions, equivalents, rearrangements, and changes in the form of the embodiments described herein may be made without departing from the spirit of the inventions described herein.

Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without operator input or prompting, whether these features, elements and/or steps are included or are to be performed in any particular embodiment. No single feature or group of features is required for or indispensable to any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The example results and parameters of the embodiments described herein are intended to illustrate and not to limit the disclosed embodiments. Other embodiments can be configured and/or operated differently than the illustrative examples described herein.

The invention claimed is:

1. A device for guiding and detecting motions of a target joint, the device comprising:
   (a) a motion generator configured to be mounted away from the target joint at an arbitrary position comprising:
      i) at least one actuator,
      ii) a driver unit in communication with the at least one actuator,
      iii) a moving component, and
      iv) a first plurality of joints interconnected with the at least one actuator, wherein a coordinated action of the at least one actuator and the first plurality of joints of the motion generator generate a three degree-of-freedom (3-DOF) rotational motion at the moving component with a first center of rotation, the first center of rotation does not coincide with a center of rotation of the target joint;
   (b) a motion transfer and target interfacing unit adapted to be functionally coupled to the moving component of the motion generator and to the target joint, the motion transfer and target interfacing unit comprising:
      i) at least one linear-motion joint comprising a sliding component and a track component, wherein the sliding component is configured to slide along the track component,
      ii) a mounting means configured to couple the motion transfer and interfacing unit to the target joint, and
      iii) one or more additional joints,
         wherein motion of the moving component of the motion generator produces synchronized responses of the one or more additional joints and the one or more linear-motion joints of the motion transfer and target interfacing unit such that the motion transfer and target interfacing unit transfers the 3-DOF rotational motion generated by the motion generator at the moving component into a corresponding 3-DOF rotational motion at the mounting means with a second center of rotation that coincides with the center of rotation of the target joint; and
   (c) a controller in communication with the motion generator and the motion transfer and target interfacing unit, the controller comprising an input unit, an output unit and a processing unit, the controller in communication with the driver unit to control the at least one actuator.

2. The device of claim 1, further comprising:
   a motion detection and feedback unit in communication with the motion generator and the controller, the motion detection and feedback unit comprising a plurality of sensors configured to detect a position and/or an orientation of the at least one actuator and the first plurality of joints of the motion generator and a position and/or an orientation of the target joint, wherein the motion detection and feedback unit feeds the detected signals of corresponding position and orientation to the controller.

3. The device of claim 1, wherein the motion transfer and target interfacing unit further comprising:
   at least one motion transfer and target interfacing unit actuator in communication with the driver unit, the controller in communication with the driver unit at least one motion transfer and target interfacing unit actuator, wherein the motion generator and the motion transfer and target interfacing unit collectively comprise at least two actuators.

4. The device of claim 1, wherein the at least one actuator is a rotary actuator or a linear actuator.

5. The device of claim 1, wherein at least one of the first plurality of joints or the one or more additional joints is a passive joint.

6. The device of claim 1, wherein the at least one actuator is lockable by the driver unit and the controller, wherein the controller in communication with the driver unit controls the locking action of the at least one actuator locking a position and/or orientation of the at least one actuator.

7. The device of claim 1, wherein at least one of the additional joints of the motion transfer and target interfacing unit is a rotary actuator and the at least one linear-motion joint of the motion transfer and target interfacing unit is an active linear actuator, the rotary actuator and the linear actuator being in communication with the driver unit.

8. The device of claim 1, wherein the target joint comprises a 3-DOF rotational joint or a quasi 3-DOF rotational joint.

9. The device of claim 8, wherein the target joint is a human joint.

10. The device of claim 9, wherein the target joint is at least one of a hip joint, a knee joint, an ankle joint, a shoulder joint, an elbow joint, a wrist joint or a finger joint.

11. The device of claim 1, wherein the mounting means comprises an orthotic and a strap.

12. The device of claim 1, wherein the at least one linear-motion joint of the motion transfer and target interfacing unit is a cylindrical joint, the cylindrical joint providing a rotating motion and a linear motion.

13. The device of claim 2, wherein the plurality of sensors comprises at least one inertial measurement unit, rotary encoder, linear encoder, rotary potentiometer, linear potentiometer, resolver, linear variable differential transformer, electromyograph, electroencephalograph, force sensor, or pressure sensor.

14. A motion capturing and force feedback system, the system comprising first and second motion guiding and detecting devices (MGDDs) for detecting and guiding motion of a respective first and second target joint of a subject, each of the first and second MGDDs comprising:
   (a) a motion generator configured to be mounted away from the target joint at an arbitrary position comprising:
      i) a first plurality of joints interconnected together;
      ii) a moving component, and
   (b) a motion transfer and target interfacing unit adapted to be functionally coupled to the moving component of the motion generator and to the corresponding target joint, the motion transfer and target interfacing unit comprising:
      i) at least one linear-motion joint comprising a sliding component and a track component, wherein the sliding component is configured to slide along the track component;
      ii) a mounting means configured to couple the motion transfer and interfacing unit to the target joint; and
      iii) one or more additional joints interconnected with the at least one linear-motion joint;
   c) a plurality of sensors in communication with the motion generator and the motion transfer and target interfacing unit of both the first and second MGDDs to detect a position and/or an orientation of the first plurality of joints and the one or more additional joints of the first and second MGDDs; and
   d) a controller in communication with the plurality of sensors the controller comprising an input unit, an output unit and a processing unit, the input unit configured to receive the input signal from the plurality of the sensors of the position and/or orientation of the first plurality of joints and the one or more additional joints of the first and second MGDDs, wherein three degree-of-freedom (3-DOF) rotational motions of the first and second target joints generate corresponding 3-DOF rotational motions at the mounting means configured to be coupled to the respective target joint with second center of rotation that coincide with the centers of rotation of the corresponding target joints, the motion transfer and target interfacing units converting such motions to the motion generators such that coordinated actions of the first plurality of joints of the motion generators generate corresponding 3-DOF motions at the moving components of the respective first and second MGDDs with first centers of rotation that do not coincide with the centers of rotation of the respective target joints, and wherein the processing unit of the controller being configured to calculate a position and/or orientation of the first and second target joints based on the position and/or orientation of the first plurality of joints of the motion generator and the one or more additional joints of the motion transfer and target interfacing unit of the respective first and second MGDDs.

15. The system of claim 14, wherein the controller comprising a first controller and a second controller, the first controller is in communication with the second controller, the first controller configured to control the motion of the first target joint and the second controller configured to control the motion of the second target joint, the first and second controllers configured to coordinate motions of the first and second target joints.

16. The system of claim 14, wherein the plurality of sensors comprises at least one inertial measurement unit, rotary encoder, linear encoder, rotary potentiometer, linear potentiometer, resolver, linear variable differential transformer, electromyograph, electroencephalograph, force sensor, or pressure sensor.

17. The system of claim 14, wherein the mounting means comprise orthotics and a strap configured to mount and secure each of the MGDDs to the subject.

18. The system of claim 14, further comprising an external Virtual Reality (VR) or an Augmented Reality (AR) system, the controller being in communication with the VR or the AR system.

19. The system of claim 18, wherein each of the first and the second MGDDs further comprising at least one actuator and a driver unit in communication with the at least one actuator, the at least one actuator and the driver being in communication to the controller, wherein the controller is configured to control the at least one actuator of each of the first and second MGDDs to resist motions of the MGDDs in one or more directions and/or one or more orientations or to apply forces to the MGDDs in one or more directions and/or orientations.

20. The system of claim 14, wherein at least one of the first or the second MGDDs further comprising at least one actuator and a driver unit in communication with the at least one actuator, the at least one actuator and the driver unit being in communication with the controller, the at least one actuator of at least one of the first or second MGDDs being configured to generate and guide at least one degree-of-freedom (1-DOF) of the respective first or second target joints.

21. The system of claim 18, wherein the controller is external and further comprising a motion detection and feedback unit in communication with the plurality of sensors to receive and store data of the position and/or orientation of the first plurality of joints and the one or more additional joints of the first and second MGDDs and transfer such data to the external controller.

22. A device for guiding and detecting motions of a target joint, the device comprising:
(a) a motion generator configured to be mounted away from the target joint at an arbitrary position comprising:
  i) a moving component; and
  ii) a plurality of joints interconnected together, wherein a coordinated action of the plurality of joints of the motion generator generate a three degree-of-freedom (3-DOF) rotational motion at the moving component with a first center of rotation, whereby the first center of rotation does not coincide with a center of rotation of the target joint; and
(b) a motion transfer and target interfacing unit adapted to be functionally coupled to the moving component of the motion generator and to the target joint, the motion transfer and target interfacing unit comprising:
  i) at least one linear-motion joint comprising a sliding component and a track component, wherein the sliding component is configured to slide along the track component,
  ii) one or more additional joints, and
  iii) a mounting means configured to couple the motion transfer and interfacing unit to the target joint,
wherein the motion transfer and target interfacing unit is configured to transfer a motion generated by the motion generator at the moving component to provide a corresponding 3-DOF rotational motion at the mounting means with a second center of rotation that coincides with the center of rotation of the target joint.

23. The device of claim 22 further comprising a plurality of sensors in communication with the motion generator and the motion transfer and target interfacing unit to detect a position and/or an orientation of the plurality of joints of the motion generator and the one or more additional joints of the motion transfer and target interfacing unit and a controller in communication with the plurality of sensors, the controller comprising an input unit, an output unit and a processing unit, the input unit configured to receive the input signal from the plurality of the sensors of the position and/or orientation of the first plurality of joints and the one or more additional joints.

24. The device of claim 22, wherein the motion generator further comprising at least one actuator, a driver unit in communication with the at least one actuator and a controller in communication with the driver unit to control the at least one actuator, the at least one actuator being applied to the plurality of joints.

25. The device of claim 22, wherein the motion transfer and target interfacing unit further comprising at least one actuator, a driver unit in communication with the at least one actuator and a controller in communication with the driver unit to control the at least one actuator, the at least one actuator being applied to at least one of the at least one linear-motion joint and the one or more additional joints.

* * * * *